US009629925B2

(12) United States Patent
Chennamsetty et al.

(10) Patent No.: US 9,629,925 B2
(45) Date of Patent: Apr. 25, 2017

(54) METHODS FOR IDENTIFICATION OF SITES FOR IGG CONJUGATION

(71) Applicants: Novartis AG, Basel (CH); Massachusetts Institute of Technology, Cambridge, MA (US)

(72) Inventors: Naresh Chennamsetty, Cambridge, MA (US); Bernhard Helk, Basel (CH); Veysel Kayser, Cambridge, MA (US); Bernhardt Trout, Cambridge, MA (US); Vladimir Voynov, Cambridge, MA (US)

(73) Assignees: Novartis AG, Basel (CH); Massachusetts Institute of Technology, Cambridge, MA (US)

( * ) Notice: Subject to any disclaimer, the term of this patent is extended or adjusted under 35 U.S.C. 154(b) by 113 days.

(21) Appl. No.: 14/449,975

(22) Filed: Aug. 1, 2014

(65) Prior Publication Data
US 2015/0056220 A1 Feb. 26, 2015

Related U.S. Application Data

(62) Division of application No. 13/375,466, filed as application No. PCT/US2010/037517 on Jun. 4, 2010, now Pat. No. 8,834,885.

(60) Provisional application No. 61/184,084, filed on Jun. 4, 2009.

(51) Int. Cl.
*A61K 39/395* (2006.01)
*C07K 16/00* (2006.01)
*C07K 16/18* (2006.01)
*A61K 47/48* (2006.01)
*A61K 51/10* (2006.01)

(52) U.S. Cl.
CPC .. *A61K 47/48507* (2013.01); *A61K 47/48384* (2013.01); *A61K 47/48438* (2013.01); *A61K 51/1093* (2013.01); *C07K 2317/522* (2013.01); *C07K 2317/524* (2013.01); *C07K 2317/526* (2013.01); *C07K 2317/56* (2013.01); *C07K 2317/567* (2013.01)

(58) Field of Classification Search
None
See application file for complete search history.

(56) References Cited

U.S. PATENT DOCUMENTS

| | | | |
|---|---|---|---|
| 6,277,375 B1 | 8/2001 | Ward | |
| 8,747,848 B2 | 6/2014 | Chennamsetty et al. | |
| 2002/0103212 A1* | 8/2002 | Serizawa | A61K 39/395 514/264.11 |
| 2005/0244403 A1 | 11/2005 | Lazar et al. | |
| 2007/0092940 A1* | 4/2007 | Eigenbrot | A61K 47/48538 435/69.1 |
| 2007/0202098 A1 | 8/2007 | Lazar et al. | |
| 2008/0050310 A1 | 2/2008 | Ebens et al. | |
| 2010/0297103 A1* | 11/2010 | Murakami | C07K 16/2863 424/130.1 |
| 2013/0053547 A1 | 2/2013 | Kai et al. | |

FOREIGN PATENT DOCUMENTS

| | | |
|---|---|---|
| CN | 1671741 A | 9/2005 |
| CN | 1958615 A | 5/2007 |
| EP | 1810979 A | 7/2007 |
| EP | 2006380 | 12/2008 |
| WO | WO-03/074679 A | 9/2003 |
| WO | WO-04/001007 A | 12/2003 |
| WO | WO-2004/001007 A2 | 12/2003 |
| WO | WO-2005/045442 A | 5/2005 |
| WO | WO-2006/034488 | 3/2006 |
| WO | WO-2007/022070 A2 | 2/2007 |
| WO | WO-2007/103288 | 9/2007 |
| WO | WO-2007/109221 A | 9/2007 |
| WO | WO2008/032833 * | 3/2008 |
| WO | WO-2008/088983 A1 | 7/2008 |

OTHER PUBLICATIONS

Hsu (1994). "The variation in immunoglobulin heavy chain constant regions in evolution," Semin Immunol. 6(6):383-91.
Putnam et al. (1981). "Amino acid sequence of the first constant region domain and the hinge region of the delta heavy chain of human IgD," Proc Natl Acad Sci U S A. 78(10):6168-72.
Abraham et al. (1987). "Extension of the fragment method to calculate amino acid zwitterion and side chain partition coefficients," Proteins: Structure, function, and genetics 130-152, p. 148.
Black et al. (1991). "Development of hydrophobicity parameters to analyze proteins which bear post- or cotranslational modifications," Anal Biochem 193:72-82.
Brard et al. (Sep. 6, 1999) "Somatic mutation and light chain rearrangement generate autoimmunity in anti-single-stranded DNA transgenic MRL/lpr mice" Journal of Experimental Medicine 190(5):691-704.
Burgess et al. (1990). "Possible dissociation of the heparin-binding and mitogenic activities of heparin-binding (acidic fibroblast) growth factor-1 from its receptor-binding activities by site-directed mutagenesis of a single lysine residue," J Cell Biol 111:2129-2138.
Cellmer et al. (May 17, 2007). "Protein aggregation in silico," *Trends in Biotechnology* 25(6):254-257.
Chennamsetty et al. (Aug. 14, 2009). "Aggregation-prone motifs in human immunoglobulin G" J Mol Biol 391(2):404-413.
Chennamsetty, N. et al. (Jul. 2009). "Design of therapeutic proteins with enhanced stability," *Proceedings of the National Academy of Sciences of the United States of America* 106(29):11937-11942.
de Groot, N.S. et al. (Sep. 30, 2005). "Prediction of hot spots of aggregation in disease-linked polypeptides," *BMC Structural Biology* 5(1):18.

(Continued)

*Primary Examiner* — Michael D Allen
(74) *Attorney, Agent, or Firm* — Morrison & Foerster LLP

(57) ABSTRACT

The present disclosure relates to immunoglobulins and immunoglobulin conjugates with reduced oligomerization and efficient labeling and compositions, methods of generating such immunoglobulins and immunoglobulin conjugates and methods of using such immunoglobulin conjugates particularly in the treatment and prevention of disease.

9 Claims, No Drawings

(56) References Cited

OTHER PUBLICATIONS

Hou et al. (2005). "An extended aqueous solvation model based on atom-weighted solvent accessible surface areas: SAWSA v2.0 model," J Mol Model. Feb. 2005;11(1):26-40.

International Preliminary Report on Patentability mailed Feb. 12, 2013, for PCT/US2009/047948, 13 pages.

International Search Report and Written Opinion mailed Jan. 25, 2013, for PCT/US2009/047948, 23 pages.

International Search Report and Written Opinion mailed Nov. 30, 2009, for PCT Application No. PCT/US2009/047954 filed Jun. 19, 2009, 20 pages.

International search report mailed Jan. 12, 2011, for PCT/US2010/037517 filed Jun. 4, 2010, 8 pages.

Jespers et al. (2004) "Aggregation-resistant domain antibodies selected on phage by heat denaturation," Nature Biotech 22:1161-1165.

Junutula et al. (Aug. 1, 2008) "Site-specific conjugation of a cytotoxic drug to an antibody improves the therapeutic index" Nature Biotechnology 26(8):925-932.

Junutula et al. (Jan. 14, 2008). "Rapid identification of reactive cysteine residues for site-specific labeling of antibody-Fabs" Journal of Immunological Methods, 332(1-2):41-52.

Kellog et al. (1991). "HINT: a new method of empirical hydrophobic field calculation for CoMFA," J Computer-Aided Molec Des 5:545-552.

Lazar et al. (1998). "Transforming growth factor alpha: mutation of aspartic acid 47 and leucine 48 results in different biological activities," Mol Cell Biol 8:1247-1252.

Lee et al. (1971). "The interpretation of protein structures: estimation of static accessibility," J Mol Biol 55:379-400.

Lu et al. (Feb. 2008). "The effect of a point mutation on the stability of IgG4 as monitored by analytical ultracentrifugation," J Pharma Sci 97(2):960-969.

Lyons et al. (Jan. 1, 1990) "Site-specific attachment to recombinant antibodies via introduced surface cysteine residues" Protein Engineering 3(8):703-708.

Nelson et al. (2000). Principles of Biochemistry, p. 1-1152.

Pawar, A.P. et al. (Jul. 8, 2005). "Prediction of 'Aggregate-prone' and 'Aggregate-susceptible' Regions in Proteins Associated with Neurodegenerative Diseases," *Journal of Molecular Biology* 350(2):379-392.

Spassov, V. et al. (1995). "The optimization of protein-solvent interactions: Thermostability and the role of hydrophobic and electrostatic interactions," *Protein Science* 4(8):1516-1527.

Stimmel et al. (Sep. 29, 2000) "Site-specific conjugation on serine-cysteine variant monoclonal antibodies" Journal of Biological Chemistry 275(39):30445-30450.

Voynov et al. (Feb. 17, 2010) "Design and application of antibody cysteine variants." Bioconjugate Chemistry 21(2):385-392.

Wesson et al. (1992). "Atomic solvation parameters applied to molecular dynamics of proteins in solution," Protein Sci 1(2):227-235.

Connolly (1983). "Solvent-accessible surfaces of proteins and nucleic acids," Science. 221(4612):709-13.

Partial European Search Report mailed Jun. 11, 2015 for EP15156284.0, 8 pages.

Nieba et al. (1997). "Disrupting the hydrophobic patches at the antibody variable/constant domain interface: improved in vivo folding and physical characterization of an engineered scFv fragment," Protein Eng. 10(4):435-44.

Patro et al. (1994)."Simulations of kinetically irreversible protein aggregate structure," Biophys J. 66(5):1274-89.

Raschke et al. (2001). "Quantification of the hydrophobic interaction by simulations of the aggregation of small hydrophobic solutes in water," Proc Natl Acad Sci U S A. 98(11):5965-9.

Russian Decision to Grant, for Russian Application No. 2011101997/10, filed Jun. 19, 2009, Decision dated Jul. 8, 2015, 20 pages (10 pages translation and 10 pages Russian Decision).

* cited by examiner

```
                              SEQUENCE LISTING

<160> NUMBER OF SEQ ID NOS: 18

<210> SEQ ID NO 1
<211> LENGTH: 103
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 2
<211> LENGTH: 103
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys
            100
```

<210> SEQ ID NO 3
<211> LENGTH: 103
<212> TYPE: PRT
<213> ORGANISM: Homo sapiens

<400> SEQUENCE: 3

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly
            100
```

<210> SEQ ID NO 4
<211> LENGTH: 103
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Pro Lys Thr Pro
            100
```

<210> SEQ ID NO 5
<211> LENGTH: 17
<212> TYPE: PRT
<213> ORGANISM: Homo sapiens

<400> SEQUENCE: 5

```
Asp Lys Thr His Thr Cys Pro Pro Cys Pro Ala Pro Glu Leu Leu Gly
  1               5                  10                  15

Gly
```

-continued

<210> SEQ ID NO 6
<211> LENGTH: 13
<212> TYPE: PRT
<213> ORGANISM: Homo sapiens

<400> SEQUENCE: 6

Val Glu Cys Pro Pro Cys Pro Ala Pro Val Ala Gly
1               5                   10

<210> SEQ ID NO 7
<211> LENGTH: 14
<212> TYPE: PRT
<213> ORGANISM: Homo sapiens

<400> SEQUENCE: 7

Pro Pro Cys Pro Ser Cys Pro Ala Pro Glu Phe Leu Gly Gly
1               5                   10

<210> SEQ ID NO 8
<211> LENGTH: 26
<212> TYPE: PRT
<213> ORGANISM: Homo sapiens

<400> SEQUENCE: 8

Leu Gly Thr Thr His Thr Cys Pro Arg Cys Pro Glu Pro Lys Cys Pro
1               5                   10                  15

Arg Cys Pro Ala Pro Glu Leu Leu Gly Gly
            20                  25

<210> SEQ ID NO 9
<211> LENGTH: 108
<212> TYPE: PRT
<213> ORGANISM: Homo sapiens

<400> SEQUENCE: 9

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu
            100                 105

<210> SEQ ID NO 10
<211> LENGTH: 108
<212> TYPE: PRT
<213> ORGANISM: Homo sapiens

<400> SEQUENCE: 10

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
            35                  40                  45

Asn Ala Lys Thr Lys Pro Arg Glu Glu Gln Phe Asn Ser Thr Phe Arg
 50                  55                  60

Val Val Ser Val Leu Thr Val Val His Gln Asp Trp Leu Asn Gly Lys
 65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys Gly Gln Pro Arg Glu
            100                 105

<210> SEQ ID NO 11
<211> LENGTH: 108
<212> TYPE: PRT
<213> ORGANISM: Homo sapiens

<400> SEQUENCE: 11

Pro Ser Val Phe Leu Phe Pro Pro Lys Pro Lys Asp Thr Leu Met Ile
 1               5                  10                  15

Ser Arg Thr Pro Glu Val Thr Cys Val Val Val Asp Val Ser Gln Glu
                20                  25                  30

Asp Pro Glu Val Gln Phe Asn Trp Tyr Val Asp Gly Val Glu Val His
            35                  40                  45

Asn Ala Lys Thr Lys Pro Arg Glu Glu Gln Phe Asn Ser Thr Tyr Arg
 50                  55                  60

Val Val Ser Val Leu Thr Val Leu His Gln Asp Trp Leu Asn Gly Lys
 65                  70                  75                  80

Glu Tyr Lys Cys Lys Val Ser Asn Lys Gly Leu Pro Ser Ser Ile Glu
                85                  90                  95

Lys Thr Ile Ser Lys Ala Lys Gly Gln Pro Arg Glu
            100                 105

<210> SEQ ID NO 12
<211> LENGTH: 108
<212> TYPE: PRT
<213> ORGANISM: Homo sapiens

<400> SEQUENCE: 12

Pro Ser Val Phe Leu Phe Pro Pro Lys Pro Lys Asp Thr Leu Met Ile
 1               5                  10                  15

Ser Arg Thr Pro Glu Val Thr Cys Val Val Val Asp Val Ser His Glu
                20                  25                  30

Asp Pro Glu Val Gln Phe Asn Trp Tyr Val Asp Gly Val Glu Val His
            35                  40                  45

Asn Ala Lys Thr Lys Pro Arg Glu Glu Gln Tyr Asn Ser Thr Tyr Arg
 50                  55                  60

Val Val Ser Val Leu Thr Val Leu His Gln Asp Trp Leu Asn Gly Lys
 65                  70                  75                  80

Glu Tyr Lys Cys Lys Val Ser Asn Lys Ala Leu Pro Ala Pro Ile Glu
                85                  90                  95

Lys Thr Ile Ser Lys Thr Lys Gly Gln Pro Arg Glu
            100                 105

<210> SEQ ID NO 13
<211> LENGTH: 102
<212> TYPE: PRT
<213> ORGANISM: Homo sapiens -continued

```
<400> SEQUENCE: 13

Pro Gln Val Tyr Thr Leu Pro Pro Ser Arg Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Val Leu Asp Ser Asp Gly Ser Phe Phe Leu Tyr Ser Lys
    50                  55                  60

Leu Thr Val Asp Lys Ser Arg Trp Gln Gln Gly Asn Val Phe Ser Cys
65                  70                  75                  80

Ser Val Met His Glu Ala Leu His Asn His Tyr Thr Gln Lys Ser Leu
                85                  90                  95

Ser Leu Ser Pro Gly Lys
            100

<210> SEQ ID NO 14
<211> LENGTH: 102
<212> TYPE: PRT
<213> ORGANISM: Homo sapiens

<400> SEQUENCE: 14

Pro Gln Val Tyr Thr Leu Pro Pro Ser Arg Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Met Leu Asp Ser Asp Gly Ser Phe Phe Leu Tyr Ser Lys
    50                  55                  60

Leu Thr Val Asp Lys Ser Arg Trp Gln Gln Gly Asn Val Phe Ser Cys
65                  70                  75                  80

Ser Val Met His Glu Ala Leu His Asn His Tyr Thr Gln Lys Ser Leu
                85                  90                  95

Ser Leu Ser Pro Gly Lys
            100

<210> SEQ ID NO 15
<211> LENGTH: 102
<212> TYPE: PRT
<213> ORGANISM: Homo sapiens

<400> SEQUENCE: 15

Pro Gln Val Tyr Thr Leu Pro Pro Ser Gln Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Val Leu Asp Ser Asp Gly Ser Phe Phe Leu Tyr Ser Arg
    50                  55                  60

Leu Thr Val Asp Lys Ser Arg Trp Gln Glu Gly Asn Val Phe Ser Cys
65                  70                  75                  80
```

```
Ser Val Met His Glu Ala Leu His Asn His Tyr Thr Gln Lys Ser Leu
                85                  90                  95

Ser Leu Ser Leu Gly Lys
            100

<210> SEQ ID NO 16
<211> LENGTH: 102
<212> TYPE: PRT
<213> ORGANISM: Homo sapiens

<400> SEQUENCE: 16

Pro Gln Val Tyr Thr Leu Pro Pro Ser Arg Glu Glu Met Thr Lys Asn
  1               5                  10                  15

Gln Val Ser Leu Thr Cys Leu Val Lys Gly Phe Tyr Pro Ser Asp Ile
             20                  25                  30

Ala Val Glu Trp Glu Ser Ser Gly Gln Pro Glu Asn Asn Tyr Lys Thr
         35                  40                  45

Thr Pro Pro Val Leu Asp Ser Asp Gly Ser Phe Phe Leu Tyr Ser Lys
     50                  55                  60

Leu Thr Val Asp Lys Ser Arg Trp Gln Gln Gly Asn Ile Phe Ser Cys
 65                  70                  75                  80

Ser Val Met His Glu Ala Leu His Asn His Phe Thr Gln Lys Ser Leu
                85                  90                  95

Ser Leu Ser Pro Gly Lys
            100

<210> SEQ ID NO 17
<211> LENGTH: 103
<212> TYPE: PRT
<213> ORGANISM: Homo sapiens

<400> SEQUENCE: 17

Lys Ala Ala Pro Ser Val Thr Leu Phe Pro Pro Ser Ser Glu Glu Leu
  1               5                  10                  15

Gln Ala Asn Lys Ala Thr Leu Val Cys Leu Ile Ser Asp Phe Tyr Pro
             20                  25                  30

Gly Ala Val Thr Val Ala Trp Lys Ala Asp Ser Ser Pro Val Lys Ala
         35                  40                  45

Gly Val Glu Thr Thr Thr Pro Ser Lys Gln Ser Asn Asn Lys Tyr Ala
     50                  55                  60

Ala Ser Ser Tyr Leu Ser Leu Thr Pro Glu Gln Trp Lys Ser His Arg
 65                  70                  75                  80

Ser Tyr Ser Cys Gln Val Thr His Glu Gly Ser Thr Val Glu Lys Thr
                85                  90                  95

Val Ala Pro Thr Glu Cys Ser
            100

<210> SEQ ID NO 18
<211> LENGTH: 105
<212> TYPE: PRT
<213> ORGANISM: Homo sapiens

<400> SEQUENCE: 18

Val Ala Ala Pro Ser Val Phe Ile Phe Pro Pro Ser Asp Glu Gln Leu
  1               5                  10                  15

Lys Ser Gly Thr Ala Ser Val Val Cys Leu Leu Asn Asn Phe Tyr Pro
             20                  25                  30
```

-continued

```
Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
            85                  90                  95

Thr Lys Ser Phe Asn Arg Gly Glu Cys
            100             105
```

METHODS FOR IDENTIFICATION OF SITES FOR IGG CONJUGATION

CROSS REFERENCE TO RELATED APPLICATIONS

This application is a Divisional of U.S. patent application Ser. No. 13/375,466, claiming an international filing date of Jun. 4, 2010; now U.S. Pat. No. 8,834,885, which is a U.S. National Phase of International Patent Application No. PCT/US2010/037517, filed Jun. 4, 2010; which claims the benefit of U.S. Provisional Patent Application No. 61/184,084, filed Jun. 4, 2009; all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 619672000210SEQLIST.txt, date recorded: Jul. 30, 2014, size: 15 KB).

FIELD OF THE INVENTION

The present disclosure relates to improved immunoglobulins and immunoglobulin conjugates.

BACKGROUND

Monoclonal antibodies are of great laboratory and therapeutic use. Antibody derivatives with engineered site-specific fluorescence or binding properties have been developed and used for many years. More recently, antibodies have been also developed as therapeutic agents, currently presenting the fastest growing class of pharmaceuticals [1]. Antibodies are multidomain proteins of two light and two heavy chains held together by disulfide bonds. The variable regions specify binding to a particular antigen, and part of the constant regions is responsible for effector functions via binding to Fc receptors on the surface of immune cells. Because of their potential in the cure of various diseases, antibodies currently constitute the most rapidly growing class of human therapeutics (Carter. Nature Reviews Immunology. 2006, 6(5), 343). Since 2001, their market has been growing at an average yearly growth rate of 35%, the highest rate among all categories of biotech drugs (S. Aggarwal. Nature. BioTech. 2007, 25 (10) 1097).

Engineering of antibody conjugates has further increased the versatility of antibody applications. In many laboratory techniques, enzymes or fluorescent probes are conjugated to antibodies to carry out an assay function, for example quantitation of antigen abundance. In cases of targeted therapy, toxic small molecules are attached to antibodies that specifically bind biomarkers on diseased cells [2-4]. Various approaches to antibody conjugation have been pursued, for example attachment to surface lysines [5], to Fc carbohydrates [6], or to partially reduced interchain disulfides [7].

Antibody conjugation to engineered surface cysteine remains a very attractive option because most antibodies do not have cysteines other than the ones consumed in intra- and interchain disulfide bonds. Small molecules can be attached at the specific site of cysteine substitution via a thiol reactive chemistry such as maleimides [8-14]. Engineering in the $C_H1$ and $C_H3$ domains has been favored to avoid interference with antigen binding of the variable regions and effector function of $C_H2$. Different criteria for successful antibody conjugation via engineered cysteines have been considered. For example, the antibody domain in which to carry out mutation, the exposure of the mutated site, the amino acid to be substituted are several of the variables to take into account. A high throughput screening approach to identifying sites suitable for cysteine engineering and conjugation has been developed [15]. Two of the most common problems associated with antibody cysteine variants are oligomerization and poor labeling. Yet, there is no universal tool for predicting whether an antibody cysteine variant will be stable and efficiently conjugated. Furthermore, cysteine variants currently exist only for the $C_L$, $C_H1$ and $C_H3$ domains [8, 9, 11, 12, 15].

Thus, there is a need for additional immunoglobulin cysteine variants that can be used in the generation of stable immunoglobulin conjugates.

SUMMARY

Described herein are improved immunoglobulins and immunoglobulin conjugates which exhibit reduced cross-linking that meet this need.

Thus one aspect includes an immunoglobulin conjugate comprising an immunoglobulin having at least one mutation at a residue selected from the group consisting of 7(VH), 20(VL), 22(VL), 25(VH), 125(CH1), 248(CH2), 254(CH2), 286(CH2), 298(CH2), and 326(CH2), wherein the at least one mutation is a substitution with a cysteine residue, and an atom or molecule, wherein the atom or molecule is conjugated to the cysteine residue. In certain embodiments, the at least one mutation is at a residue selected from the group consisting of 7(VH), 20(VL), 22(VL) and 125(CH1). In certain embodiments, the at least one mutation is at a residue selected from the group consisting of 248(CH2) and 326(CH2). In certain embodiments, the at least one mutation is at a residue selected from the group consisting of 25(VH) and 286(CH2). In certain embodiments, the at least one mutation is at residue selected from the group consisting of 254(CH2) and 298(VH). In certain embodiments that may be combined with the preceding embodiments, the immunoglobulin is selected from the group comprising IgG1, IgG2, IgG3, and IgG4. In certain embodiments that may be combined with the preceding embodiments, the immunoglobulin comprises an IgG1. In certain embodiments that may be combined with the preceding embodiments, the immunoglobulin conjugate comprises a human CH1 domain. In certain embodiments that may be combined with the preceding embodiments, the immunoglobulin conjugate comprises a human CH2 domain. In certain embodiments that may be combined with the preceding embodiments, the immunoglobulin conjugate comprises a human CH3 domain. In certain embodiments that may be combined with the preceding embodiments, the immunoglobulin conjugate comprises a human CL domain. In certain embodiments that may be combined with the preceding embodiments, the immunoglobulin conjugate comprises a human VH domain. In certain embodiments that may be combined with the preceding embodiments, the immunoglobulin conjugate comprises a human VL domain. In certain embodiments that may be combined with the preceding embodiments, the immunoglobulin conjugate further comprises a linker molecule having at least two reactive sites, wherein a first reactive site is bound to the cysteine residue of the immunoglobulin and a second reactive site is bound to the atom or molecule. In certain embodiments that may be combined with the preceding embodiments having a linker molecule, the linker molecule is selected from the group consisting of a hydrazone, a disulfide, a peptide, a chelating agent, and a maleimide. In certain embodiments that may be combined with the preceding embodiments, the atom or molecule is selected from the group consisting of a radionuclide, a chemotherapeutic agent, a microbial toxin, a plant toxin, a polymer, a carbohydrate, a cytokine, a fluorescent label, a luminescent label, an enzyme-substrate label, an enzyme, a peptide, a peptidomimetic, a nucleotide, an siRNA, a microRNA, an RNA mimetic, and an aptamer. In certain embodiments that may be combined with the preceding embodiments, the atom or molecule is selected from the group consisting of 90Y, 131I, 67Cu, 177Lu, 213Bi, 211At, a calicheamicin, a duocarmycin, a maytanisoid, an auristatin, an anthracyclin, Pseudomonas exotoxin A, Diphtheria toxin, ricin, polyethylene glycol, hydroxyethyl starch, and a mannosyl residue. In certain embodiments that may be combined with the preceding embodiments, the atom or molecule reduces the immunogenicity of the unmutated immunoglobulin. In certain embodiments that may be combined with the preceding embodiments, the atom or molecule increases the immunogenicity of the unmutated immunoglobulin. In certain embodiments that may be combined with the preceding embodiments, the immunoglobulin conjugate further comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

Another aspect includes a modified or isolated immunoglobulin comprising at least one mutation at a residue selected from the group consisting of 7($V_H$), 20($V_L$), 22($V_L$), 25($V_H$), 125($C_{H1}$), 248($C_{H2}$), 254($C_{H2}$), 286($C_{H2}$), and 326($C_{H2}$), wherein the at least one mutation is a substitution with a cysteine residue. In certain embodiments, the at least one mutation is at a residue selected from the group consisting of 7($V_H$), 20($V_L$), 22($V_L$) and 125($C_{H1}$). In certain embodiments, the at least one mutation is at a residue selected from the group consisting of 248($C_{H2}$) and 326 ($C_{H2}$). In certain embodiments, the at least one mutation is at a residue selected from the group consisting of 25($V_H$) and 286($C_{H2}$). In certain embodiments, the at least one mutation is at residue 254($C_{H2}$). In certain embodiments that may be combined with the preceding embodiments, the immunoglobulin is selected from the group comprising IgG1, IgG2, IgG3, and IgG4. In certain embodiments that may be combined with the preceding embodiments, the immunoglobulin comprises an IgG1. In certain embodiments that may be combined with the preceding embodiments, the modified or isolated immunoglobulin comprises a human $C_{H1}$ domain. In certain embodiments that may be combined with the preceding embodiments, the modified or isolated immunoglobulin comprises a human $C_{H2}$ domain. In certain embodiments that may be combined with the preceding embodiments, the modified or isolated immunoglobulin comprises a human $C_{H3}$ domain. In certain embodiments that may be combined with the preceding embodiments, the modified or isolated immunoglobulin comprises a human $C_L$ domain. In certain embodiments that may be combined with the preceding embodiments, the modified or isolated immunoglobulin comprises a human $V_H$ domain. In certain embodiments that may be combined with the preceding embodiments, the modified or isolated immunoglobulin comprises a human $V_L$ domain. In certain embodiments that may be combined with the preceding embodiments, the immunoglobulin further comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

Another aspect includes isolated or recombinant polynucleotides that encode the immunoglobulins of the preceding modified immunoglobulin aspect and any and all combinations of the preceding embodiments. In certain embodiments, the polynucleotide is in a vector. In certain embodiments, the vector is an expression vector. In certain embodiments that may be combined with the preceding embodiments, an inducible promoter is operably linked to the polynucleotide. Another aspect includes host cells with the vector of either of the preceding embodiments. In certain embodiments, the host cells are capable of expressing the immunoglobulin encoded by the polynucleotide.

Another aspect includes methods of producing an immunoglobulin comprising providing a culture medium comprising the host cell of the preceding aspect and placing the culture medium in conditions under which the immunoglobulin is expressed. In certain embodiments, the methods include an additional step of isolating the immunoglobulin expressed.

Another aspect includes methods of producing an immunoglobulin conjugate comprising providing the immunoglobulin of the preceding modified immunoglobulin aspect and any and all combinations of the preceding embodiments, reducing the one or more substituted cysteine residues with a reducing agent to form reduced cysteine residues, and incubating the immunoglobulin with an atom or molecule, wherein the atom or molecule is reactive with the reduced cysteine residues, to form an immunoglobulin conjugate.

Another aspect includes methods for reducing the cross-linking between surface-exposed cysteines of an immunoglobulin in a highly concentrated pharmaceutical formulation of immunoglobulin conjugates comprising providing an immunoglobulin, substituting a residue selected from the group consisting of 7($V_H$), 20($V_L$), 22($V_L$), and 125($C_{H1}$) with a cysteine residue, reducing the one or more substituted cysteine residues with a reducing agent to form reduced cysteine residues, incubating the immunoglobulin with an atom or molecule, wherein the molecule is reactive with the reduced cysteine residues, to form an immunoglobulin conjugate, and generating a highly concentrated, liquid formulation of the immunoglobulin conjugate wherein the immunoglobulin conjugate concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is selected from the group comprising IgG1, IgG2, IgG3, and IgG4. In certain embodiments, the immunoglobulin comprises an IgG1. In certain embodiments that may be combined with the preceding embodiments, the immunoglobulin comprises a human $C_{H1}$ domain. In certain embodiments that may be combined with the preceding embodiments, the immunoglobulin comprises a human $C_{H2}$ domain. In certain embodiments that may be combined with the preceding embodiments, the immunoglobulin comprises a human $C_{H3}$ domain. In certain embodiments that may be combined with the preceding embodiments, the immunoglobulin comprises a human $C_L$ domain. In certain embodiments that may be combined with the preceding embodiments, the immunoglobulin comprises a human $V_H$ domain. In certain embodiments that may be combined with the preceding embodiments, the immunoglobulin comprises a human $V_L$ domain. In certain embodiments that may be combined with the preceding embodiments, the immunoglobulin conjugate comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

Another aspect includes uses of the preceding immunoglobulin conjugate aspect and any and all combinations of the preceding embodiments in the preparation of a medicament comprising a highly concentrated liquid formulation wherein the immunoglobulin conjugate is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the use of the medicament is for the treatment of autoimmune diseases, immunological diseases, infectious diseases, inflammatory diseases, neurological diseases, and oncological and neoplastic diseases including cancer. In certain embodiments, the use of the medicament is for the treatment of congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases. In certain embodiments, the use of the medicament is for the treatment of plaque psoriasis, ulcerative colitis, non-Hodgkin's lymphoma, breast cancer, colorectal cancer, juvenile idiopathic arthritis, macular degeneration, respiratory syncytial virus, Crohn's disease, rheumatoid arthritis, psoriatic arthritis, ankylosing spondylitis, osteoporosis, treatment-induced bone loss, bone metastases, multiple myeloma, Alzheimer's disease, glaucoma, and multiple sclerosis. In certain embodiments that may be combined with the preceding embodiments, the medicament further comprises a pharmaceutically acceptable excipient. In certain embodiments that may be combined with the preceding embodiments, the formulation comprises at least eighty percent, at least eighty-five percent, at least ninety percent, at least ninety-five percent, at least ninety-six percent, at least ninety-seven percent, at least ninety-eight percent, or at least ninety-nine percent of the immunoglobulin conjugate is non-oligomerized monomer. In certain embodiments, the percentage of monomers is measured by non-reducing SDS-PAGE analysis.

Another aspect includes uses of the preceding immunoglobulin conjugate aspect and any and all combinations of the preceding embodiments as a non-oligomerizing pharmaceutical active ingredient.

Another aspect includes uses of the preceding immunoglobulin conjugate aspect and any and all combinations of the preceding embodiments as a diagnostic tool.

Another aspect includes uses of the preceding immunoglobulin conjugate aspect and any and all combinations of the preceding embodiments as a standard for high molecular weight proteins. Another aspect includes uses of an immunoglobulin conjugate as a standard for high molecular weight proteins, wherein the immunoglobulin conjugate comprises an immunoglobulin having at least one mutation at residue 440($C_{H3}$), wherein the at least one mutation is a substitution with a cysteine residue, and an atom or molecule, wherein the atom or molecule is conjugated to the cysteine residue.

Another aspect includes pharmaceutical compositions that include an immunoglobulin conjugate of the preceding immunoglobulin conjugate aspect and any and all combinations of the preceding embodiments and a pharmaceutically acceptable excipient. In certain embodiments, the immunoglobulin conjugate is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the immunoglobulin conjugate is non-oligomerized monomer.

Another aspect includes methods for selecting a residue of an immunoglobulin for mutation to cysteine comprising calculating the Spatial-Aggregation-Propensity of a first amino acid residue on the surface of the immunoglobulin, calculating the Spatial-Aggregation-Propensities of a plurality of residues of the immunoglobulin within immediate proximity of the first residue, and selecting the first amino acid residue for mutation to cysteine if the Spatial-Aggregation-Propensity of the first amino acid residue is equal to or in between the values of 0 and −0.11 and if the plurality of residues have Spatial-Aggregation-Propensities of less than 0. In certain embodiments, the plurality of residues is within 15 Å of the first residue. In certain embodiments, the plurality of residues is within 10 Å of the first residue. In certain embodiments, the plurality of residues is within 7.5 Å of the first residue. In certain embodiments, the plurality of residues is within 5 Å of the first residue. In certain embodiments that may be combined with the preceding embodiments, calculating the Spatial-Aggregation-Propensity of a residue comprises calculating the Spatial-Aggregation-Propensity for a spherical region with a radius centered on an atom in the residue. In certain embodiments, the radius of the spherical region is at least 5 Å.

Another aspect includes modified or isolated immunoglobulins comprising at least one mutation of a surface-exposed residue to cysteine, wherein the Spatial-Aggregation-Propensity of the residue is equal to or in between the values of 0 and –0.11 and wherein the Spatial-Aggregation-Propensities of a plurality of residues of the immunoglobulin within immediate proximity of the first residue have Spatial-Aggregation-Propensities of less than 0. In certain embodiments, the plurality of residues is within 15 Å of the first residue. In certain embodiments, the plurality of residues is within 10 Å of the first residue. In certain embodiments, the plurality of residues is within 7.5 Å of the first residue. In certain embodiments, the plurality of residues is within 5 Å of the first residue. In certain embodiments that may be combined with the preceding embodiments, the Spatial-Aggregation-Propensity is calculated for a spherical region with a radius centered on an atom in the residue. In certain embodiments, the radius is at least 5 Å.

Another aspect includes methods of selecting a residue of an immunoglobulin for mutation to cysteine comprising choosing a plurality of amino acid residues of the immunoglobulin, wherein the plurality of residues are exposed on the surface of the immunoglobulin, mutating one residue of the plurality of residues to a cysteine residue, conjugating the cysteine residue to an atom or molecule to form an immunoglobulin conjugate, testing the immunoglobulin conjugate for cross-linking propensity and assigning the immunoglobulin conjugate a cross-linking propensity value, and selecting the residue for mutation to cysteine if the cross-linking propensity value is I or II. In certain embodiments, the method further comprises assigning the immunoglobulin conjugate a cross-linking propensity value of II if less than 5% of the immunoglobulin conjugate forms dimers and none of the immunoglobulin conjugate forms trimers wherein dimer and trimer formation is measured by comparative non-reducing and reducing SDS-PAGE. In certain embodiments, the method further comprises assigning the immunoglobulin conjugate a cross-linking propensity value of I if less than 1% of the immunoglobulin conjugate forms dimers wherein dimer formation is measured by comparative non-reducing and reducing SDS-PAGE.

Additional aspects and embodiments of the invention may be found throughout the specification.

DETAILED DESCRIPTION OF THE PREFERRED EMBODIMENTS

The present disclosure relates to improved immunoglobulins and immunoglobulin conjugates which exhibit reduced cross-linking. In certain embodiments, the immunoglobulins of the disclosure are modified at specific residues by substitution with cysteine. The disclosure provides modified immunoglobulins and immunoglobulin conjugates, methods of making such immunoglobulins and immunoglobulin conjugates, multivalent or multispecific molecules comprising such immunoglobulins and pharmaceutical compositions containing the immunoglobulins, immunoglobulin conjugates or bispecific molecules of the disclosure.

DEFINITIONS

The term "antibody" or "immunoglobulin" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "antibody conjugate" or "immunoglobulin conjugate" as referred to herein include any immunoglobulin, antigen binding fragment, or single chains thereof chemically or biologically linked to an atom or molecule. Atoms or molecules may include, for example, a cytotoxin, radioactive agent, anti-tumor drug, or therapeutic agent. The antibody conjugate retains the immunoreactivity of the immunoglobulin or antigen binding fragment, i.e., the immunoglobulin or antigen binding fragment of the antibody conjugate has at least seventy percent, at least seventy-five percent, at least eighty percent, at least eighty-five percent, at least ninety percent, at least ninety-five percent, at least at least one hundred percent, at least one hundred ten percent, at least one hundred twenty percent, or at least one hundred thirty percent of the antigen binding activity of the immunoglobulin prior to conjugation with the atom or molecule.

The term "antigen-binding portion" of an antibody (or simply "antigen portion"), as used herein, refers to full length or one or more fragments of an antibody that retain the ability to specifically bind to an antigen and at least a portion of the constant region of the heavy or light chain. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and $C_{H1}$ domains; a F(ab)2 fragment, a bivalent fragment comprising two Fab fragments linked by a disulfide bridge at the hinge region; a Fd fragment consisting of the $V_H$ and $C_{H1}$ domains; and a Fv fragment consisting of the $V_L$ and $V_H$ domains of a single arm of an antibody.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated" antibody or immunoglobulin, as used herein, refers to an antibody or immunoglobulin that is substantially free of other components in which such antibodies or immunoglobulin are naturally found. Moreover, an isolated antibody or immunoglobulin may be substantially free of other cellular material and/or chemicals.

The terms "monoclonal antibody" or "monoclonal antibody composition" as used herein refer to a preparation of antibody molecules of single molecular composition. A monoclonal antibody composition typically displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. (2000. J Mol Biol 296, 57-86).

The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human domain", as used herein, is intended to include immunoglobulin constant region domains derived from sequences of human origin, e.g., human germline sequences, or mutated versions of human germline sequences or antibody containing consensus framework sequences derived from human framework sequences analysis as described in Knappik, et al. (2000. J Mol Biol 296, 57-86).

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin comprising a modification as disclosed herein. Due to the replacement with a human constant region, the chimeric antibody can retain its specificity while having reduced antigenicity in human and reduced aggregation overall as compared to the original mouse antibody or a chimeric antibody without the modification as disclosed herein.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun, 31:169-217, 1994. Other examples of human engineering technology include, but are not limited to Xoma technology disclosed in U.S. Pat. No. 5,766,886.

The term "linker", "linker Unit", or "link" as used herein refers to a chemical moiety comprising a covalent bond or a chain of atoms that covalently attaches an antibody to a drug moiety or other molecule. Linkers include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, polyetheramine (JEFFAMINE™)); and diacid ester and amides including succinate, succinamide, diglycolate, malonate, and caproamide.

The term "label" as used herein refers to any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The term "Humaneering" as used herein refers to a method for converting non-human antibodies into engineered human antibodies (See e.g., KaloBios' Humaneering™ technology).

As used herein, "isotype" refers to any antibody class (e.g., IgM, IgE, IgG such as IgG1 or IgG2) that is provided by the heavy chain constant region genes that have the aggregation prone motifs disclosed herein (and therefore are amenable to the modifications disclosed herein that reduce aggregation).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. The modifications disclosed herein preferably do not reduce the affinity of the immunoglobulin or antibodies disclosed herein or the affinity is reduced less than thirty percent, less than twenty percent, less than ten percent, or less than five percent. As used herein, when determining whether the modifications disclosed herein reduce affinity the comparison is made between the immunoglobulin or antibody with the modification and the same immunoglobulin lacking the modification but including any unrelated mutations.

As used herein, the term "subject" includes any human or nonhuman animal.

The term "nonhuman animal" includes all vertebrates, e.g., mammals and non-mammals, such as nonhuman primates, sheep, dogs, cats, horses, cows, chickens, amphibians, reptiles, etc.

The term "chemotherapeutic agent" as used herein refers to a chemical compound useful in the treatment of cancer. Examples of chemotherapeutic agents include Erlotinib (TARCEVA™, Genentech/OSI Pharm.), Bortezomib (VELCADE™, Millenium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (ELOXATIN™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as thiotepa and CYTOXAN™ cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; (ii) aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestanie, fadrozole, RIVISOR™ vorozole, FEMARA™ letrozole, and ARIMIDEX™ anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYME™ ribozyme) and a HER2 expression inhibitor; (ix) vaccines such as gene therapy vaccines, for example, ALLOVEC-TIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

As used herein, the term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. Optimized expression of these sequences in other eukaryotic cells is also envisioned herein. The amino acid sequences encoded by optimized nucleotide sequences are also referred to as optimized.

As used herein, the term "antigen binding activity" refers to the specificity of binding of an immunoglobulin or immunoglobulin conjugate to its target antigen. For example, antigen binding activity may be measured by cell-based bioassays (e.g. reporter gene assays), ELISA, surface plasmon resonance (Biacore), or any other techniques known to one skilled in the art.

As used herein, the term "cross-linking propensity" (CLP) refers to the propensity of a modified immunoglobulin or immunoglobulin conjugate containing a mutation that is a substitution with cysteine to cross-link between different immunoglobulins at the substituted cysteine residue. For example, CLP can be determined by the level of oligomerization as measured by non-reducing SDS-PAGE, size-exclusion chromatography, static or dynamic laser light scattering with size-exclusion chromatography, or any other techniques known to one skilled in the art. Class I comprises variants that are monomeric and remain stable after labeling. Variants of class II contain a small percent of dimers before and after labeling. Class III variants have a more pronounced propensity to oligomerize including formation of some trimers. Class IV variants have even higher propensity to oligomerize as evidenced by the presence of aggregates larger than trimer, especially after labeling. Class V includes variants of high oligomerization propensity similarly to variant of Class IV with additional structural abnormalities such as fragmentation or coloration of purified concentrated sample.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "target antigen" refers to the antigen against which the parent immunoglobulin was raised or otherwise generated (e.g., by phage display).

The term "unmutated immunoglobulin" refers to the immunoglobulin which does not comprise the at least one mutation that is a substitution with a cysteine residue. As used herein, the unmutated immunoglobulin may be a hypothetical construct for the purposes of comparison of the oligomerization propensity or the conjugation efficiency of the immunoglobulin with and without the mutation. By way of example, a murine antibody that includes humanizing mutations as well as mutations to cysteine for the purpose of conjugation is not the unmutated immunoglobulin. The unmutated immunoglobulin would be the antibody with the humanizing mutations, but without the mutations to cysteine. Where a mutation is intended to serve more than one purpose including providing sites for conjugation, the unmutated immunoglobulin does not include such mutation.

The term "aggregation motif" refers to a set of residues grouped together based upon the following process. First, residues having an SAP (5 Å radius) of greater than 0.15 are identified. Then all residues within 5 Å of each residue having an SAP (5 Å radius) of greater than 0.15 are identified. A motif is then the residue with an SAP (5 Å radius) of greater than 0.15 and all residues with an SAP (5 Å radius) of greater than 0.0 within 5 Å of the residue with an SAP (5 Å radius) of greater than 0.15. Any such motifs having at least one residue in common are merged into a larger motif reiteratively until there are no remaining motifs which have a residue in common. These remaining motifs or sets of residues constitute aggregation motifs.

Where immunoglobulin residues are referred to by number herein, the residue number refers to the Kabat number of the corresponding residue in the IgG1 molecule when the immunoglobulin sequence of interest is aligned to the human IgG1 immunoglobulin. By way of reference, the human IgG1, IgG2, IgG3 and IgG4 constant domains are aligned:

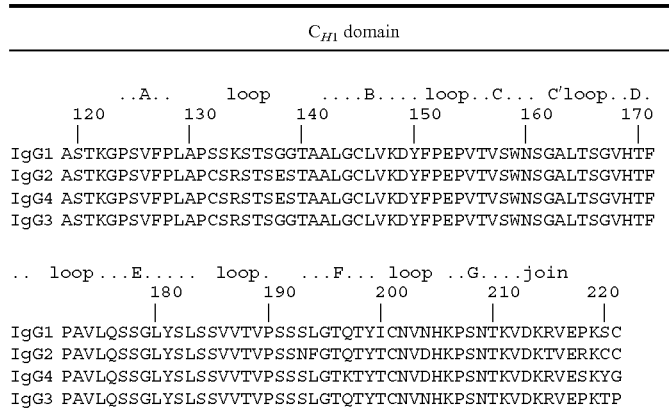

(IgG1 = SEQ ID NO: 1; IgG2 = SEQ ID NO: 2; IgG4 = SEQ ID NO: 3; IgG3 = SEQ ID NO: 4)

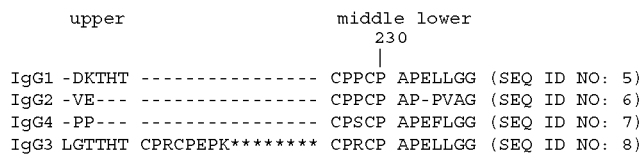

-continued

$C_{H2}$ domain

```
           ..A..   loop    ....B....  loop  ..C..    C'loop   ...D
           240     250     260        270   280              290
           |       |       |          |     |                |
IgG1 PSVFLFPPKPKDTLMISRTPEVTCVVVDVSHEDPEVKFNWYVDGVEVHNAKTKP
IgG2 PSVFLFPPKPKDTLMISRTPEVTCVVVDVSHEDPEVQFNWYVDGVEVHNAKTKP
IgG4 PSVFLFPPKPKDTLMISRTPEVTCVVVDVSQEDPEVQFNWYVDGVEVHNAKTKP
IgG3 PSVFLFPPKPKDTLMISRTPEVTCVVVDVSHEDPEVQFNWYVDGVEVHNAKTKP ... loop    ....E...  .loop.  ...F.....loop ..G...  joinC3
             300           310     320           330     340
             |             |       |             |       |
IgG1 REEQYNSTYRVVSVLTVLHQDWLNGKEYKCKVSNKALPAPIEKTISKAKGQPRE
IgG2 REEQFNSTFRVVSVLTVVHQDWLNGKEYKCKVSNKGLPAPIEKTISKTKGQPRE
IgG4 REEQFNSTYRVVSVLTVLHQDWLNGKEYKCKVSNKGLPSSIEKTISKAKGQPRE
IgG3 REEQYNSTYRVVSVLTVLHQDWLNGKEYKCKVSNKALPAPIEKTISKTKGQPRE
```

(IgG1 = SEQ ID NO: 9; IgG2 = SEQ ID NO: 10;
IgG4 = SEQ ID NO: 11; IgG3 = SEQ ID NO: 12)

$C_{H3}$ domain

```
         ..A..   loop    ....B....  loop  ..C...C'loop..D....
         350     360     370        380   390              400
         |       |       |          |     |                |
IgG1 PQVYTLPPSREEMTKNQVSLTCLVKGFYPSDIAVEWESNGQPENNYKTTPPVLDS
IgG2 PQVYTLPPSREEMTKNQVSLTCLVKGFYPSDIAVEWESNGQPENNYKTTPPMLDS
IgG4 PQVYTLPPSQEEMTKNQVSLTCLVKGFYPSDIAVEWESNGQPENNYKTTPPVLDS
IgG3 PQVYTLPPSREEMTKNQVSLTCLVKGFYPSDIAVEWESSGQPENNYKTTPPVLDS loop  ....E...  .loop.   ...F...  loop  ....G....
           410       420      430            440
           |         |        |              |
IgG1 DGSFFLYSKLTVDKSRWQQGNVFSCSVMHEALHNHYTQKSLSLSPGK
IgG2 DGSFFLYSKLTVDKSRWQQGNVFSCSVMHEALHNHYTQKSLSLSPGK
IgG4 DGSFFLYSRLTVDKSRWQEGNVFSCSVMHEALHNHYTQKSLSLSLGK
IgG3 DGSFFLYSKLTVDKSRWQQGNIFSCSVMHEALHNHFTQKSLSLSPGK
```

(IgG1 = SEQ ID NO: 13; IgG2 = SEQ ID NO: 14;
IgG4 = SEQ ID NO: 15; IgG3 = SEQ ID NO: 16)

$C_L$ domain

```
                    11        12         13         14         15
                    0123456789012345678901234567890123456789
constant  •  KAAPSVTLFPPSSEELQANKATLVCLISDFYPGAVTVAWK
constant  •  VAAPSVFIFPPSDEQLKSGTASVVCLLNNFYPREAKVQWK 16        17         18         19
                    0123456789012345678901234567890123456789
constant  •  ADSSPVKAGVETTTPSKQS-NNKYAASSYLSLTPEQWKSH
constant  •  VDNALQSGNSQESVTEQDSKDSTYSLSSTLTLSKADYEKH 20         21
                    012345678901234567890123456
constant  •  RSYSCQVTHEG--STVEKTVAPTECS  (SEQ ID NO: 17)
constant  •  KVYACEVTHQGLSSPVTKSFNRGEC   (SEQ ID NO: 18)
```

Alignments of the $V_H$ and $V_L$ domains can be found in Ewert, Honegger, and Plúchthun, *Methods* 34 (2004) 184-199.

Immunoglobulin Conjugates of the Invention

The invention herein relates to immunoglobulin conjugates including immunoglobulins having at least one mutation of a residue of the surface of the immunoglobulin wherein the mutation is a substitution with a cysteine residue. The substituted cysteine residue is conjugated to an atom or molecule, which may be, by way of example, a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent. In further embodiments, the molecule may be an enzyme, a peptide, a peptidomimetic, a nucleotide such as an RNA molecule, including siRNA, microRNA, and RNA mimetics, or aptamers.

Labeled Immunoglobulin Conjugates

In certain embodiments, modified immunoglobulins of the invention may be conjugated with any label moiety which can be covalently attached to the immunoglobulin through a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function, for example, to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labeled immunoglobulin conjugates may be useful in diagnostic assays, e.g., for detecting expression of an antigen of interest in specific cells, tissues, or serum. For diagnostic applications, the immunoglobulin will typically be labeled with a detectable moiety. Numerous labels are available which can be generally grouped into the following exemplary categories:

(a) Radioisotopes (radionuclides), such as $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Radioisotope labeled immunoglobulins are useful in receptor targeted imaging experiments. The immunoglobulin can be labeled with ligand reagents that bind, chelate or otherwise complex a radioisotope metal where the reagent is reactive with the engineered cysteine thiol of the immunoglobulin, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9):1137-1146).

Metal-chelate complexes suitable as immunoglobulin labels for imaging experiments are disclosed: U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to immunoglobulins using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

Examples of enzyme-substrate combinations include, for example: (i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); (ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase. Numerous other enzyme-substrate combinations are available to those skilled in the art. For a general review, see U.S. Pat. Nos. 4,275,149 and 4,318,980.

A label may be indirectly conjugated with modified immunoglobulins of the invention. For example, the immunoglobulin can be conjugated with biotin and any of the three broad categories of labels mentioned above can be conjugated with avidin or streptavidin, or vice versa. Biotin binds selectively to streptavidin and thus, the label can be conjugated with the immunoglobulin in this indirect manner. Alternatively, to achieve indirect conjugation of the label with the immunoglobulin variant, the immunoglobulin variant is conjugated with a small hapten (e.g., digoxin) and one of the different types of labels mentioned above is conjugated with an anti-hapten polypeptide variant (e.g., anti-digoxin antibody). Thus, indirect conjugation of the label with the immunoglobulin variant can be achieved (Hermanson, G. (1996) in Bioconjugate Techniques Academic Press, San Diego).

The modified immunoglobulins and immunoglobulin conjugates of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labeled immunoglobulin conjugates of the invention can detect cell-surface receptors. Another use for detectably labeled immunoglobulin conjugates is a method of bead-based immunocapture comprising conjugating a bead with a fluorescent labeled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labeling immunoglobulins, preferably with the following properties: (i) the labeled immunoglobulin should produce a very high signal with low background so that small quantities of immunoglobulins can be sensitively detected in both cell-free and cell-based assays; and (ii) the labeled antibody should be photostable so that the fluorescent signal may be observed, monitored and recorded without significant photo bleaching. For applications involving cell surface binding of labeled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labeled events, e.g. cell surface binding of peptide-dye conjugates may be conducted on an system (FMAT™ 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labeled immunoglobulins also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labeled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labeled immunoglobulin conjugates of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from pre-clinical (small animal) to clinical (human) results. For some applications, bioimaging supplants or minimizes the number of animal experiments in preclinical studies.

Radionuclide imaging labels include radionuclides such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. The radionuclide metal ion can be complexed with a chelating linker such as DOTA. Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the modified immunoglobulins and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labeled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labeled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labeled antibodies of the invention may also be used as an affinity purification agent. In this process, the labeled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labelling reagents typically bear reactive functionality which may react (i) directly with a cysteine thiol of a modified immunoglobulin to form the labeled antibody, (ii) with a linker reagent to form a linker-label intermediate, or (iii) with a linker antibody to form the labeled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

It is accordingly an object of the present invention to provide uses of the immunoglobulin conjugates as discussed in paragraph [0007] and any and all combinations of their embodiments as a diagnostic tool.

It is accordingly an object of the present invention to provide uses of the immunoglobulin conjugates as discussed in paragraph [0007] and any and all combinations of their embodiments as a standard for high molecular weight proteins.

Immunoglobulin Polymer Conjugates

In further embodiments, the present invention also contemplates immunoglobulin conjugates, in which an immunoglobulin is linked with a polymer. Typically, the polymer is water soluble so that an immunoglobulin component does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-($C_1$-$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce conjugates with antibody components.

Suitable water-soluble polymers include, without limitation, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers.

As an illustration, a polyalkyl oxide moiety can be attached to the N-terminus of an immunoglobulin component. PEG is one suitable polyalkyl oxide. For example, an immunoglobulin can be modified with PEG, a process known as "PEGylation." PEGylation of an immunoglobulin can be carried out by any of the PEGylation reactions known in the art (see, for example, EP 0 154 316, Delgado et al., Critical Reviews in Therapeutic Drug Carrier Systems 9:249 (1992), Duncan and Spreafico, Clin. Pharmacokinet. 27:290 (1994), and Francis et al., Int J Hematol 68:1 (1998)). For example, PEGylation can be performed by an acylation reaction or by an alkylation reaction with a reactive polyethylene glycol molecule. In an alternative approach, immunoglobulin conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an immunoglobulin. An example of an activated PEG ester is PEG esterified to N-hydroxysuccinimide. As used herein, the term "acylation" includes the following types of linkages between an immunoglobulin and a water soluble polymer: amide, carbamate, urethane, and the like. Methods for preparing PEGylated anti-B CMA-TACI immunoglobulins by acylation will typically comprise the steps of (a) reacting an immunoglobulin with PEG (such as a reactive ester of an aldehyde derivative of PEG) under conditions whereby one or more PEG groups attach to the immunoglobulin, and (b) obtaining the reaction product(s). Generally, the optimal reaction conditions for acylation reactions will be determined based upon known parameters and desired results. For example, the larger the ratio of PEG: antibody component, the greater the percentage of polyPEGylated antibody component product.

The product of PEGylation by acylation is typically a polyPEGylated immunoglobulin product, wherein the lysine s-amino groups are PEGylated via an acyl linking group. An example of a connecting linkage is an amide. Typically, the resulting immunoglobulin component will be at least 95% mono-, di-, or tri-pegylated, although some species with higher degrees of PEGylation may be formed depending upon the reaction conditions. PEGylated species can be separated from unconjugated immunoglobulin components using standard purification methods, such as dialysis, ultrafiltration, ion exchange chromatography, affinity chromatography, and the like.

PEGylation by alkylation generally involves reacting a terminal aldehyde derivative of PEG with an immunoglobulin component in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the s-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups.

Reductive alkylation to produce a substantially homogenous population of monopolymer antibody component conjugate molecule can comprise the steps of: (a) reacting an antibody component with a reactive PEG under reductive alkylation conditions at a pH suitable to permit selective modification of the α-amino group at the amino terminus of the antibody component, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer immunoglobulin conjugates, the reductive alkylation reaction conditions are those which permit the selective attachment of the water soluble polymer moiety to the N-terminus of the immunoglobulin. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: antibody component need not be as large because more reactive groups are available. Typically, the pH will fall within the range of 3 to 9, or 3 to 6.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., Clin. Pharmacol. Ther. 59:636 (1996), Monkarsh et al., Anal Biochem. 247:434 (1997)).

Immunoglobulin Drug Conjugates

In further embodiments, the present invention includes immunoglobulin conjugates in which an immunoglobulin is conjugated to a drug or cytotoxic moiety. The drug moiety of the immunoglobulin drug conjugates may, for example, include any compound, moiety or group which has a cytotoxic or cytostatic effect. Drug moieties include, without limitation: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl) +/−C-19-dechloro (U.S. Pat. Nos. 4,361, 650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424, 219) (prepared by the reaction of maytansinol with $H_2S$ or $P_2S_5$); C-14-alkoxymethyl(demethoxy/$CH_2OR$)(U.S. Pat. No. 4,331,598); C-14-hydroxymethyl or acyloxymethyl ($CH_2OH$ or $CH_2OAc$) (U.S. Pat. No. 4,450,254) (prepared from Nocardia); C-l 5-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

Maytansine compounds inhibit cell proliferation by inhibiting the formation of microtubules during mitosis through inhibition of polymerization of the microtubulin protein, tubulin (Remillard et al (1975) Science 189:1002-1005). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207).

Maytansinoid drug moieties are attractive drug moieties in immunoglobulin drug conjugates because they are: (i)

relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines (US 2005/0169933; WO 2005/037992; U.S. Pat. No. 5,208,020).

As with other drug moieties, all stereoisomers of the maytansinoid drug moiety are contemplated for the compounds of the invention.

The drug moiety of the immunoglobulin drug conjugates also include dolastatins and their peptidic analogs and derivatives, the auristatins (U.S. Pat. Nos. 5,635,483; 5,780, 588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102(4):1458-1465).

Exemplary auristatin embodiments include the N-terminus linked monomethylauristatin drug moieties DE and DF, disclosed in: WO 2005/081711; Senter et al, Proceedings of the American Association for Cancer Research, Volume 45, Abstract Number 623, presented Mar. 28, 2004, the disclosure of each which are expressly incorporated by reference in their entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Luibke, "The Peptides", volume 1, pp 76-136, 1965, Academic Press) that is well known in the field of peptide chemistry.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701, 5,770,710; 5,773,001; 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al Cancer Research 53:3336-3342 (1993), Lode et al Cancer Research 58:2925-2928 (1998).

Protein toxins include, for example, diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes (WO 93/21232).

Therapeutic radioisotopes include, for example, $^{32}P$, $^{33}P$, $^{90}Y$, $^{125}I$, $^{131}I$, $^{131}In$, $^{153}Sm$, $^{186}Re$, $^{188}Re$, $^{211}At$, $^{212}Bi$, $^{212}Pb$, and radioactive isotopes of Lu.

The radioisotope or other labels may be incorporated in the conjugate in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triaminepentaacetic acid (MX-DTPA) is an exemplary chelating agent for conjugation of a radionuclide to the antibody (WO 94/11026).

Linkers

In certain embodiments of the present invention, the immunoglobulin conjugate includes a linker molecule having at least two reactive sites. One reactive site is bound to the substituted cysteine residue of the immunoglobulin, and the other reactive site is bound to an atom or molecule. A "linker" is a bifunctional or multifunctional moiety which can be used to link one or more drug moieties and an immunoglobulin unit to form immunoglobulin conjugates. Immunoglobulin conjugates can be conveniently prepared using a linker having reactive functionality for binding to the drug or other molecule and to the immunoglobulin. A cysteine thiol of a modified immunoglobulin with a substitution to cysteine can form a bond with a functional group of a linker reagent, a drug moiety or drug-linker intermediate.

In one aspect, a linker has a reactive site which has an electrophilic group that is reactive to a nucleophilic cysteine present on an antibody. The cysteine thiol of the antibody is reactive with an electrophilic group on a linker and forms a covalent bond to a linker. Useful electrophilic groups include, but are not limited to, maleimide and haloacetamide groups.

Modified immunoglobulins of the invention react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773.

The linker may comprise amino acid residues. The amino acid unit, when present, links the immunoglobulin to the drug moiety of the immunoglobulin drug conjugates of the invention.

The amino acid linker may be, for example, a dipeptide, tripeptide, tetrapeptide, pentapeptide, hexapeptide, heptapeptide, octapeptide, nonapeptide, decapeptide, undecapeptide or dodecapeptide unit Amino acid residues which comprise the amino acid unit include those occurring naturally, as well as minor amino acids and non-naturally occurring amino acid analogs, such as citrulline.

The Amino Acid unit can be enzymatically cleaved by one or more enzymes, including a tumor-associated protease, to liberate the drug moiety.

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the immunoglobulin drug conjugate. Thus, where a modified immunoglobulin bears only one reactive cysteine thiol group, a multitude of drug moieties may be attached through a dendritic linker.

In another embodiment, the linker may be substituted with groups which modulated solubility or reactivity. For example, a charged substituent such as sulfonate ($-SO_3^-$) or ammonium, may increase water solubility of the reagent and facilitate the coupling reaction of the linker reagent with the immunoglobulin or the drug moiety, or facilitate the coupling reaction of the immunoglobulin-linker intermediate with the drug moiety, or the drug-linker intermediate with the immunoglobulin, depending on the synthetic route employed to prepare the immunoglobulin conjugate.

The compounds of the invention expressly contemplate, but are not limited to, immunoglobulin conjugates prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 U.S.A, U.S.A 1-800-874-3723, International +815-968-0747. See pages 467-498, 2003-2004 Applications Handbook and Catalog. Bis-maleimide reagents allow the attachment of the thiol group of a cysteine to a thiol-containing drug moiety, label, or linker intermediate, in a sequential or concurrent fashion. Other functional groups besides maleimide, which are reactive with a thiol group of a cysteine, drug moiety, label, or linker intermediate include, without limitation, iodoacetamide, bromoacetamide, vinyl pyridine, disulfide, pyridyl disulfide, isocyanate, and isothiocyanate.

It is accordingly an object of the present invention to provide immunoglobulin conjugates comprising an immunoglobulin having at least one mutation at a residue selected from the group consisting of 7($V_H$), 20($V_L$), 22($V_L$), 25($V_H$), 125($C_{H1}$), 248($C_{H2}$), 254($C_{H2}$), 286($C_{H2}$), 298 ($C_{H2}$), and 326($C_{H2}$), wherein the at least one mutation is a substitution with a cysteine residue, and an atom or molecule, wherein the atom or molecule is conjugated to the cysteine residue. In certain embodiments, the at least one mutation is at a residue selected from the group consisting of 7($V_H$), 20($V_L$), 22($V_L$) and 125($C_{H1}$). In certain embodiments, the at least one mutation is at a residue selected from the group consisting of 248($C_{H2}$) and 326($C_{H2}$). In certain embodiments, the at least one mutation is at a residue selected from the group consisting of 25($V_H$) and 286($C_{H2}$). In certain embodiments, the at least one mutation is at residue selected from the group consisting of 254($C_{H2}$) and 298($V_H$). In certain embodiments that may be combined with the preceding embodiments, the immunoglobulin is selected from the group comprising IgG1, IgG2, IgG3, and IgG4. In certain embodiments that may be combined with the preceding embodiments, the immunoglobulin comprises an IgG1. In certain embodiments that may be combined with the preceding embodiments, the immunoglobulin conjugate comprises a human $C_{H1}$ domain. In certain embodiments that may be combined with the preceding embodiments, the immunoglobulin conjugate comprises a human $C_{H2}$ domain. In certain embodiments that may be combined with the preceding embodiments, the immunoglobulin conjugate comprises a human $C_{H3}$ domain. In certain embodiments that may be combined with the preceding embodiments, the immunoglobulin conjugate comprises a human $C_L$ domain. In certain embodiments that may be combined with the preceding embodiments, the immunoglobulin conjugate comprises a human $V_H$ domain. In certain embodiments that may be combined with the preceding embodiments, the immunoglobulin conjugate comprises a human $V_L$ domain. In certain embodiments that may be combined with the preceding embodiments, the immunoglobulin conjugate further comprises a linker molecule having at least two reactive sites, wherein a first reactive site is bound to the cysteine residue of the immunoglobulin and a second reactive site is bound to the atom or molecule. In certain embodiments that may be combined with the preceding embodiments having a linker molecule, the linker molecule is selected from the group consisting of a hydrazone, a disulfide, a peptide, a chelating agent, and a maleimide. In certain embodiments that may be combined with the preceding embodiments, the atom or molecule is selected from the group consisting of a radionuclide, a chemotherapeutic agent, a microbial toxin, a plant toxin, a polymer, a carbohydrate, a cytokine, a fluorescent label, a luminescent label, an enzyme-substrate label, an enzyme, a peptide, a peptidomimetic, a nucleotide, an siRNA, a microRNA, an RNA mimetic, and an aptamer. In certain embodiments that may be combined with the preceding embodiments, the atom or molecule is selected from the group consisting of $^{90}$Y, $^{131}$I, $^{67}$Cu, $^{177}$Lu, $^{213}$Bi, $^{211}$At, a calicheamicin, a duocarmycin, a maytanisoid, an auristatin, an anthracyclin, *Pseudomonas* exotoxin A, Diphtheria toxin, ricin, polyethylene glycol, hydroxyethyl starch, and a mannosyl residue. In certain embodiments that may be combined with the preceding embodiments, the atom or molecule reduces the immunogenicity of the unmutated immunoglobulin. In certain embodiments that may be combined with the preceding embodiments, the atom or molecule increases the immunogenicity of the unmutated immunoglobulin. In certain embodiments that may be combined with the preceding embodiments, the immunoglobulin conjugate further comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

It is accordingly an object of the present invention to provide modified or isolated immunoglobulins comprising at least one mutation at a residue selected from the group consisting of 7($V_H$), 20($V_L$), 22($V_L$), 25($V_H$), 125($C_{H1}$), 248($C_{H2}$), 254($C_{H2}$), 286($C_{H2}$), and 326($C_{H2}$), wherein the at least one mutation is a substitution with a cysteine residue. In certain embodiments the at least one mutation is at a residue selected from the group consisting of 7($V_H$), 20($V_L$), 22($V_L$) and 125($C_{H1}$). In certain embodiments the at least one mutation is at a residue selected from the group consisting of 248($C_{H2}$) and 326($C_{H2}$). In certain embodiments the at least one mutation is at a residue selected from the group consisting of 25($V_H$) and 286($C_{H2}$). In certain embodiments the at least one mutation is at residue 254 ($C_{H2}$). In certain embodiments that may be combined with the preceding embodiments, the immunoglobulin is selected from the group comprising IgG1, IgG2, IgG3, and IgG4. In certain embodiments that may be combined with the preceding embodiments, the immunoglobulin comprises an IgG1. In certain embodiments that may be combined with the preceding embodiments, the modified or isolated immunoglobulin comprises a human $C_{H1}$ domain. In certain embodiments that may be combined with the preceding embodiments, the modified or isolated immunoglobulin comprises a human $C_{H2}$ domain. In certain embodiments that may be combined with the preceding embodiments, the modified or isolated immunoglobulin comprises a human $C_{H3}$ domain. In certain embodiments that may be combined with the preceding embodiments, the modified or isolated immunoglobulin comprises a human $C_L$ domain. In certain embodiments that may be combined with the preceding embodiments, the modified or isolated immunoglobulin comprises a human $V_H$ domain. In certain embodiments that may be combined with the preceding embodiments, the modified or isolated immunoglobulin comprises a human $V_L$ domain. In certain embodiments that may be combined with the preceding embodiments, the immunoglobulin further comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

Preparation of Immunoglobulin Drug Conjugates

In one aspect, the present invention includes methods of producing immunoglobulin conjugates. The immunoglobulin drug conjugate may be prepared by several routes, employing organic chemistry reactions, conditions, and reagents known to those skilled in the art, including: (1) reaction of a cysteine group of a modified immunoglobulin with a linker reagent, to form an immunoglobulin-linker intermediate, via a covalent bond, followed by reaction with an activated drug moiety; and (2) reaction of a nucleophilic group of a drug moiety with a linker reagent, to form a drug-linker intermediate, via a covalent bond, followed by reaction with a cysteine group of a modified immunoglobulin. Conjugation methods (1) and (2) may be employed with a variety of modified immunoglobulins, drug moieties, and linkers to prepare the immunoglobulin drug conjugates of the invention.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Maytansine may, for example, be converted to May-SSCH$_3$, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163, 5,208,020, 5,416,064; WO 01/024763). The disulfide linker SPP is constructed with linker reagent N-succinimidyl 4-(2-pyridylthio)pentanoate.

Under certain conditions, the modified immunoglobulins may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.) or other reducing agents known to one of skill in the art.

It is accordingly an object of the present invention to provide methods of producing immunoglobulin conjugates by providing modified or isolated immunoglobulins as discussed in paragraphs [0008] or [0019] and any and all combinations of their embodiments, reducing the one or more substituted cysteine residues with a reducing agent to form reduced cysteine residues, and incubating the immunoglobulin with an atom or molecule, wherein the atom or molecule is reactive with the reduced cysteine residues, to form an immunoglobulin conjugate.

Spatial-Aggregation-Propensity

In one aspect, the invention herein relates to methods for selecting residues on a protein surface to mutate to cysteine and for reducing cross-linking of a modified immunoglobulin or immunoglobulin conjugate. The invention may be applied to generate immunoglobulins and immunoglobulin conjugates with reduced propensity for cross-linking, i.e., the immunoglobulin or immunoglobulin conjugate in concentrated solution remains primarily in monomeric form rather than higher order aggregated multimers. The methods herein represent an advancement in the ability of computational methods to evaluate the propensity of a protein to cross-link. In particular, the methods are based, at least in part, on the calculation of the SAA (Solvent Accessible Area), which is known in the art for characterizing the surface of a protein. SAA gives the surface area of each amino acid or protein structure that is in contact with the solvent. SAA may be typically calculated by computing the locus of the center of a probe sphere as it rolls over the protein surface, i.e., the surface of a protein structural model. The probe sphere has the same radius as that of a water molecule, R=1.4 Å. Alternative methods of calculating SAA, described below, are known in the art and are compatible with the methods described herein. Although SAA is quite useful to characterize the protein surface, it was not found to be adequate to characterize the hydrophobic patches on the protein surface that are potentially aggregation prone because of the following shortcomings, 1. SAA doesn't distinguish between hydrophobic and hydrophilic regions
2. SAA is not directly proportional to a residue's hydrophobicity (for example, MET has more surface area than LEU but is less hydrophobic)
3. SAA doesn't indicate whether several hydrophobic residues are close-by and thus could enhance the hydrophobicity of a certain region. These residues could be close-by either in primary sequence or in the tertiary structure even though they are far in primary sequence. Either way, they could enhance the hydrophobicity of a certain patch on the antibody surface.

One measure which is described herein, the Effective-SAA, is generated by calculating the hydrophobicity of the fraction of the amino acid which is exposed according to the formula below:

$$\text{Effective-}SAA = \frac{SAA}{SAA_{fully\ exposed}} \times \text{Residue hydrophobicity}$$

A further embodiment of the Effective-SAA further comprises summing the Effective-SAA over at least two, at least three, at least four, at least five or at least six, (e.g., two, three, four, five, six, etc.) amino acid residues which are adjacent in the primary protein sequence. Although the Effective-SAA represents an improvement over the basic SAA, it nevertheless lacks the ability to fully account for the structure of the folded protein and for the fact that amino acids which are not adjacent in the protein sequence may be in proximity to one another in the folded secondary, tertiary, or quaternary structure of a protein. Such protein folds may form aggregation prone regions which do not appear in the primary structure alone, or which may only be detected by more robustly analyzing the folded protein structure.

The present invention provides a new, more advanced measure, called the Spatial-Aggregation-Propensity, which will highlight the effective hydrophobicity of a certain patch or region on the protein surface. The Spatial-Aggregation-Propensity is calculated for defined spatial regions on or near the atoms of a protein structural model.

In this context, a "defined spatial region" is a three-dimensional space or volume chosen to capture a local physical structure and/or chemical environment on or near the protein structure. In a particularly preferred embodiment the Spatial-Aggregation-Propensity is calculated for spherical regions with radius R centered on atoms in a protein (e.g., atoms in a protein structural model). The Spatial-Aggregation-Propensity may also be calculated for spherical regions with radius R centered on chemical bonds, or positioned in space near the structural model. Accordingly, in another embodiment the SAP may be calculated for a defined spatial region centered near an atom, e.g., centered on a point in space which is between 1-10 Å, 1-5 Å, or 1-2 Å from the center of a particular atom or chemical bond.

In certain embodiments, the chosen radius R is between 1 Å and 50 Å. In particular embodiments the chosen radius is at least 1 Å, at least 3 Å, at least 4 Å, at least 5 Å, at least 6 Å, at least 7 Å, at least 8 Å, at least 9 Å, at least 10 Å, at least 11 Å, at least 12 Å, at least 15 Å, at least 20 Å, at least 25 Å, or at least 30 Å. In certain embodiments, the chosen radius is between 5 Å and 15 Å, between 5 Å and 12 Å, or between 5 Å and 10 Å. In specific embodiments the chosen radius is 5 Å or 10 Å.

In other embodiments, the region for which the Spatial-Aggregation-Propensity is calculated is not spherical. The possible shape of the region may further comprise a cube, a cylinder, a cone, an elliptical spheroid, a pyramid, a hemisphere, or any other shape which may be used to enclose a portion of space. In such embodiments, the size of the region may be chosen using measures other than radius, e.g., the distance from the center of the shape to a face or vertex.

In a certain embodiment, the SAP may be used to select residues in a protein, particularly an antibody or immunoglobulin, which may be substituted with cysteine without increasing the protein's propensity to cross-link. The present invention is expected to streamline the process of identifying residues that can be substituted with cysteine without increasing the propensity for cross-linking.

Thus, in general terms, a method for calculating the Spatial-Aggregation-Propensity for a particular atom in a protein comprises (a) identifying one or more atoms in a structural model representing the protein, wherein the one or more atoms are within a defined spatial region centered on or near the particular atom; (b) calculating, for each of the one or more atoms in the defined spatial region, a ratio of the solvent accessible area (SAA) of the atoms to the SAA of atoms in an identical residue which is fully exposed; (c) multiplying each ratio by the atom hydrophobicity of the one or more atoms; and (d) summing the products of step (c); whereby the sum is the SAP for the particular atom.

In a related embodiment, the SAP may be calculated according to a different method comprising (a) identifying one or more amino acid residues in a structural model representing the protein, wherein the one or more amino acid residues have at least one atom within a defined spatial region centered on or near the particular atom; (b) calculating, for each of the identified one or more amino acid residues, a ratio of the solvent accessible area (SAA) of atoms in the amino acid to the SAA of atoms in an identical residue which is fully exposed; (c) multiplying each ratio by the hydrophobicity of the one or more amino acid residues as determined by an amino acid hydrophobicity scale; and (d) summing the products of step (c); whereby the sum is the SAP for the particular atom. In preferred embodiments, the structural model is processed prior to step (a) by allowing the structural model to interact with solvent in a molecular dynamics simulation. When an amino acid is identified as having at least one atom within the defined spatial region, the at least one atom may be required to be exclusively an atom in an amino acid side chain. Alternatively it may be an atom required to be a main chain atom.

In other embodiments, this method may further comprise optionally conducting a molecular dynamics simulation prior to step (a) and repeating steps (a)-(d), each time conducting a further molecular dynamics simulation at a plurality of time steps, thereby producing multiple sums as in step (d), and calculating the average of the sums; whereby the calculated average is the SAP for the particular atom.

One of skill in the art will appreciate that an embodiment of the present invention which employs the average of values calculated over a molecular dynamics simulation will be more computationally intensive. Such an embodiment will also, in some cases, provide a more precise or highly resolved map of the Spatial-Aggregation-Propensity. However, experiments discussed herein have shown that the method is still highly accurate when the molecular dynamics averaging is not employed. In one preferred embodiment, Spatial-Aggregation-Propensity values may be calculated for all protein structures in a database, e.g., the Protein Data Bank (PDB), thereby swiftly identifying hydrophobic residues and patches on all known protein structures. This method allows rapid screening of large sets of proteins to identify potential aggregation prone regions and/or protein interaction sites.

In a preferred application, the Spatial-Aggregation-Propensity is described by the following formula:

$$SAP_{atom} = \Sigma_{Simulation\ Average}(\Sigma_{atoms\ within\ R\ of\ atom}((SAA\text{-}R/SAA\text{-}fe)*atom\text{-}hb)$$

wherein:
1) SAA-R is SAA of side chain atoms within radius R which is computed at each simulation snapshot. SAA is preferably calculated in the simulation model by computing the locus of the center of a probe sphere as it rolls over the protein surface. The probe sphere has the same radius as that of a water molecule, R=1.4 A. One of skill in the art will appreciate that other methods of computing the SAA would be compatible with the methods described here to calculate SAP. For example, the SAA may be calculated on only amino acid side chain atoms. The SAA may also be calculated on only amino acid main chain atoms (i.e., those atoms of the peptide backbone and associated hydrogens). Alternatively, the SAA may be calculated on only amino acid main chain atoms with the exclusion of associated hydrogens;
2) SAA-fe is SAA of side chain of fully exposed residue (say for amino acid 'X') which is obtained, in a preferred embodiment, by calculating the SAA of side chains of the middle residue in the fully extended conformation of tripeptide 'Ala-X-Ala'; and
3) atom-hb is Atom Hydrophobicity which is obtained as described above using the hydrophobicity scale of Black and Mould (Black and Mould, *Anal. Biochem.* 1991, 193, 72-82). The scale is normalized such that Glycine has a hydrophobicity of zero. Therefore, amino acids that are more hydrophobic than Glycine are positive and less hydrophobic than Glycine are negative on the hydrophobic scale.

A residue which is "fully exposed" is a residue, X, in the fully extended conformation of the tripeptide Ala-X-Ala. One of skill in the art will appreciate that this arrangement is designed such that a calculation of SAA on such a residue, X, will yield the maximum solvent accessible area available. Accordingly, it is contemplated that other residues besides alanine may be used in the calculation without wholly disrupting or altering the results.

As described above, the methods of the present invention may be applied to any protein structural model including an X-ray structure using the same formula as above.

Similarly, if the X-ray structure is not available, the same Spatial-Aggregation-Propensity parameter can be applied to the structure generated through homology modeling, and the SAP parameter may be calculated using the same formula as above.

In certain embodiments the Spatial-Aggregation-Propensity is calculated for all atoms in a protein structural model. In some embodiments, the atomistic Spatial-Aggregation-Propensity values may be averaged over each individual protein residue, or over small groups of residues.

Uses of the SAP Methodology

In one aspect, the present invention may be used as described above to identify hydrophobic amino acid residues, regions or patches in a protein. Without wanting to be held to specific threshold values, atoms or amino acid residues having a Spatial-Aggregation-Propensity >0 are considered to be hydrophobic, or to be in an aggregation prone region. Depending on the type of protein, the particular structure, and the solvent in which it exists, it may be desirable to identify atoms or residues using a cutoff which is slightly below zero, e.g., by choosing atoms or residues which have a Spatial-Aggregation-Propensity of greater than −0.1, −0.15, −0.2, etc. Alternatively, it may be desirable to employ a more stringent cutoff, e.g., 0, 0.05, 0.1, 0.15, 0.2, etc., in order to choose the strongest hydrophobic atoms, residues, or patches. In addition, as the algorithm gives higher numbers to residues at the center of a patch, residues within 3 Å, 4 Å, 5 Å, 7.5 Å, or 10 Å of the residue meeting the cutoff can also be selected for mutation to less hydrophobic residues to reduce aggregation. In another embodiment, it may be advantageous simply to select atoms or residues having Spatial-Aggregation-Propensity which is larger than atoms or residues which are nearby either sequentially (i.e., along the protein sequence) or, in a preferred embodiment, spatially (i.e., in the three-dimensional structure). One preferred method for selecting atoms or residues in a hydrophobic patch is to map the calculated Spatial-Aggregation-Propensity values, e.g., using a color coding or numerical coding, onto the protein structural model from which they were derived, thus visualizing differences in the Spatial-Aggregation-Propensity across the protein surface and hence allowing easy selection of hydrophobic patches or residues. In a particularly preferred embodiment, the calculations for Spatial-Aggregation-Propensity are carried out separately using two values chosen for the radius, one of higher resolution, e.g., 5 Å, and one of lower resolution, e.g., 10 Å. In such an embodiment larger or broader hydrophobic patches may be seen on the protein structure with the lower resolution map. Once hydrophobic patches of interest are selected on the low resolution map, those patches may be viewed in greater detail in the higher resolution map which may, in some embodiments, allow one of skill in the art to more easily or more accurately choose residues to mutate or modify. For example, when viewing a hydrophobic patch in the higher resolution map, it may be desirable to select for mutation the residue which has the highest SAP score or is the most hydrophobic (e.g., the most hydrophobic residue in the patch according to the scale of Black and Mould, *Anal. Biochem.* 1991, 193, 72-82).

In a specific embodiment a method to identify an aggregation prone region on a protein comprises (a) mapping onto the structural model the SAP as calculated according to any of the methods described herein for atoms in the protein; and (b) identifying a region within in the protein having a plurality of atoms having a SAP>0; wherein the aggregation prone region comprises the amino acids comprising said plurality of atoms. In such an embodiment the SAP may be calculated for all the atoms in a protein or a portion of the atoms. It is contemplated that one may only calculate the SAP for particular residues or groups of residues which are of interest.

In a similar embodiment, it may be informative to plot the SAP scores of the atoms (or the SAP score as averaged over amino acid residues). Such a plot showing the SAP score along the atoms or residues of a protein allows the easy identification of peaks, which may indicate candidates for replacement. In a particularly preferred embodiment the SAP scores along the atoms or residues in the protein are plotted in a graph and the Area Under the Curve (AUC) is calculated for peaks in the graph. In such an embodiment, peaks with a larger AUC represent larger or more hydrophobic aggregation prone regions. In particular embodiments it will be desirable to select for replacement one or more residues which are identified as existing in a peak, or, more preferably, in a peak with a large AUC.

In particular embodiments the present invention may be used to select a residue of an immunoglobulin for mutation to cysteine. As used herein, the SAP value of a first amino acid residue on the surface of an immunoglobulin is calculated. If the SAP value is equal to or in between the values of 0 and −0.11, the first residue is selected for mutation to cysteine. In a further embodiment, the SAP values of a plurality of residues of the immunoglobulin within immediate proximity of the first residue are calculated. If the plurality of residues has SAP values of less than 0, the first residue is selected for mutation to cysteine.

Immunoglobulin variants may be made by any method known in the art including site directed mutagenesis and other recombinant DNA technology, e.g., see U.S. Pat. Nos. 5,284,760; 5,556,747; 5,789,166; 6,878,531, 5,932,419; and, 6,391,548.

In particular embodiments the present invention may be used to make an immunoglobulin variant which can be conjugated to an atom or molecule by replacing at least one amino acid residue exposed on the surface of the immunoglobulin identified by any of the methods described herein with a natural amino acid residue, a modified amino acid residue, an unusual amino acid residue, an unnatural amino acid residue, or an amino acid analog or derivative which can be used for conjugating the immunoglobulin to an atom or molecule. In preferred embodiments, the amino acid residue exposed on the surface of the immunoglobulin is replaced with cysteine. In other embodiments, the amino acid residue is replaced with lysine, aspartate, or pyrorlysine.

The synthesis of unnatural amino acids is known to those of skill in the art, and is further described, e.g., in U.S. Patent Publication No. 2003-0082575. In general, any method known in the art to synthesize or incorporate unnatural, modified, or unusual amino acids into proteins may be employed including, but not limited to those methods described or referenced in the publications Liao J. *Biotechnol Prog.* 2007 January-February; 23(1):28-31; Rajesh, and Iqbal. *Curr Pharm Biotechnol.* 2006 August; 7(4):247-59; Cardillo et al. *Mini Rev Med Chem.* 2006 March; 6(3):293-304; Wang et al. *Annu Rev Biophys Biomol Struct.* 2006; 35:225-49; Chakraborty et al., *Glycoconj J.* 2005 March; 22(3):83-93. As a further example, the Ambrx ReCODE™ technology may be employed to develop and incorporate unnatural amino acids, or unusual amino acids into proteins as indicated by the methods described herein.

Immunoglobulin variants and immunoglobulin conjugates according to the invention can exhibit enhanced or improved stability as determined, for example, by non-reducing SDS-PAGE.

It is accordingly an object of the present invention to provide isolated or recombinant polynucleotides that encode modified immunoglobulins as discussed in paragraphs [0008] and [0019] and any and all combinations of their embodiments. In certain embodiments, the polynucleotide is in a vector. In certain embodiments, the vector is an expression vector. In certain embodiments that may be combined with the preceding embodiments, an inducible promoter is operably linked to the polynucleotide. Another aspect includes host cells with the vector of either of the preceding embodiments. In certain embodiments, the host cells are capable of expressing the immunoglobulin encoded by the polynucleotide.

It is accordingly an object of the present invention to provide methods of producing an immunoglobulin with a reduced propensity for cross-linking comprising providing a culture medium comprising the host cell of the preceding paragraph and placing the culture medium in conditions under which the immunoglobulin is expressed. In certain embodiments, the methods include an additional step of isolating the immunoglobulin expressed.

It is accordingly an object of the present invention to provide methods for selecting a residue of an immunoglobulin for mutation to cysteine comprising calculating the Spatial-Aggregation-Propensity of a first amino acid residue on the surface of the immunoglobulin, calculating the Spatial-Aggregation-Propensities of a plurality of residues of the immunoglobulin within immediate proximity of the first residue, and selecting the first amino acid residue for mutation to cysteine if the Spatial-Aggregation-Propensity of the first amino acid residue is equal to or in between the values of 0 and −0.11 and if the plurality of residues have Spatial-Aggregation-Propensities of less than 0. In certain embodiments, the plurality of residues is within 15 Å of the first residue. In certain embodiments, the plurality of residues is within 10 Å of the first residue. In certain embodiments, the plurality of residues is within 7.5 Å of the first residue. In certain embodiments, the plurality of residues is within 5 Å of the first residue. In certain embodiments that may be combined with the preceding embodiments, calculating the Spatial-Aggregation-Propensity of a residue comprises calculating the Spatial-Aggregation-Propensity for a spherical region with a radius centered on an atom in the residue. In certain embodiments, the radius of the spherical region is at least 5 Å.

In some embodiments, the invention further relates to computer code for determining SAP according to the methods of the invention. In other embodiments, the invention relates to a computer, a supercomputer, or cluster of computers dedicated to performing the methods of the invention. In yet another aspect, the invention provides a web-based, server based, or internet based service for selecting residues of a protein to mutate to cysteine, the service comprising accepting data about a protein (e.g., a protein structural model) from a user (e.g., over the internet) or retrieving such data from a database such that the service provider can generate, retrieve, or access a static structure of the protein, optionally including molecular dynamics modeling of the protein to provide a dynamic structure of the protein, determining SAP for atoms or residues of the protein based on the static or dynamic structure so generated, and returning the SAP data, for example, as a structural model mapped with said SAP data by the service provider, to a user. In some embodiments, the user is a person. In other embodiments the user is a computer system or automated computer algorithm.

In some embodiments the present invention proves an SAP calculation system comprising: a web server for providing a web service for calculating SAP to a user terminal through the Internet; a database for storing general information on the calculation method, amino acid hydrophobicity, etc., and a calculation server for performing the SAP calculation based on information in the database and information provided or transmitted through the internet by the user.

In some embodiments, the web server and the calculation server are the same computer system. In some embodiments the computer system is a supercomputer, a cluster computer, or a single workstation or server. In a related embodiment the web server of the SAP calculation system further comprises a controller for controlling the entire operation, a network connection unit for connection to the Internet, and a web service unit for providing a web service for calculating SAP to the user terminal connected through the Internet.

In addition, embodiments of the present invention further relate to computer storage products with a computer readable medium that contain program code for performing various computer-implemented operations, e.g., calculating the SAP for a structural model, calculating SAA, calculating effective-SAA, manipulating structural models, implementing molecular dynamics simulations, organizing and storing relevant data, or performing other operations described herein. The computer-readable medium is any data storage device that can store data which can thereafter be read by a computer system. Examples of computer-readable media include, but are not limited to hard disks, floppy disks, flash drives, optical discs (e.g., CDs, DVDs, HD-DVDs, Blu-Ray discs, etc.) and specially configured hardware devices such as application specific integrated circuits (ASICs) or programmable logic devices (PLDs). The computer-readable medium can also be distributed as a data signal embodied in a carrier wave over a network of coupled computer systems so that the computer readable code is stored and executed in a distributed fashion. It will be appreciated by those skilled in the art that the above described hardware and software elements are of standard design and construction. The computer, internet, server, and service related embodiments described above may further apply to the SAA and the effective-SAA as well as SAP.

Pharmaceutical Compositions Containing Immunoglobulins and Immunoglobulin Conjugates In another aspect, the present invention provides a composition, e.g., a pharmaceutical composition, containing one or more immunoglobulin conjugates produced by the methods of the invention, formulated together with a pharmaceutically acceptable carrier. Pharmaceutical compositions of the invention also can be administered in combination therapy, i.e., combined with other agents. For example, the combination therapy can include an immunoglobulin conjugate of the present invention combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the immunoglobulin or variant thereof of the invention, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Exemplary formulations comprise at least one immunoglobulin variant of the invention and can comprise lower concentrations of stabilizing (or disaggregation) agents which can, in addition to the methods disclosed herein, be used to prevent or diminish aggregation of an immunoglobulin. Accordingly, conventional methods used to prevent aggregation may be employed in the development of pharmaceutical compositions containing immunoglobulin variants produced by the methods of the present invention. For example, a variety of stabilizing or disaggregating compounds may be included in pharmaceutical compositions of the invention depending on their intended use and their biological toxicity. Such stabilizing compounds may include, for example, cyclodextrin and its derivatives (U.S. Pat. No. 5,730,969), alkylglycoside compositions (U.S. patent application Ser. No. 11/474,049), the use of chaperone molecules (e.g., LEA (Goyal et al., Biochem J. 2005, 388(Pt 1):151-7; the methods of U.S. Pat. No. 5,688,651), betaine compounds (Xiao, Burn, Tolbert, Bioconjug Chem. 2008 May 23), surfactants (e.g., Pluronic F127, Pluronic F68, polysorbate 20 (TWEEN 20™) (Wei et al. International Journal of Pharmaceutics. 2007, 338(1-2):125-132)), and the methods described in U.S. Pat. Nos. 5,696,090, 5,688,651, and 6,420,122.

In addition, proteins, and in particular antibodies, are stabilized in formulations using combinations of different classes of excipients, e.g., (1) disaccarides (e.g. Saccharose, Trehalose) or polyols (e.g. Sorbitol, Mannitol) act as stabilizers by preferential exclusion and are also able to act as cryoprotectants during lyophilization, (2) surfactants (e.g. Polysorbat 80, Polysorbat 20) act by minimizing interactions of proteins on interfaces like liquid/ice, liquid/material-surface and/or liquid/air interfaces and (3) buffers (e.g. phosphate-, citrate-, histidine) help to control and maintain formulation pH. Accordingly, such disaccharides polyols, surfactants and buffers may be used in addition to the methods of the present invention to further stabilize immunoglobulins and prevent their aggregation.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

It is accordingly an object of the present invention to provide methods for reducing the cross-linking between surface-exposed cysteines of an immunoglobulin in a highly concentrated pharmaceutical formulation of immunoglobulin conjugates comprising providing an immunoglobulin, substituting a residue selected from the group consisting of $7(V_H)$, $20(V_L)$, $22(V_L)$, and $125(C_{H1})$ with a cysteine residue, reducing the one or more substituted cysteine residues with a reducing agent to form reduced cysteine residues, incubating the immunoglobulin with an atom or molecule, wherein the molecule is reactive with the reduced cysteine residues, to form an immunoglobulin conjugate, and generating a highly concentrated, liquid formulation of the immunoglobulin conjugate wherein the immunoglobulin conjugate concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is selected from the group comprising IgG1, IgG2, IgG3, and IgG4. In certain embodiments, the immunoglobulin comprises an IgG1. In certain embodiments that may be combined with the preceding embodiments, the immunoglobulin comprises a human $C_{H1}$ domain. In certain embodiments that may be combined with the preceding embodiments, the immunoglobulin comprises a human $C_{H2}$ domain. In certain embodiments that may be combined with the preceding embodiments, the immunoglobulin comprises a human $C_{H3}$ domain. In certain embodiments that may be combined with the preceding embodiments, the immunoglobulin comprises a human $C_L$ domain. In certain embodiments that may be combined with the preceding embodiments, the immunoglobulin comprises a human $V_H$ domain. In certain embodiments that may be combined with the preceding embodiments, the immunoglobulin comprises a human $V_L$ domain. In certain embodiments that may be combined with the preceding embodiments, the immunoglobulin conjugate comprises an antigen binding activity and the activity is at least eighty percent, at least ninety percent, at least one hundred percent, at least one hundred ten percent, at least one hundred twenty percent, or at least one hundred thirty percent of the antigen binding activity of the unmutated immunoglobulin.

It is accordingly an object of the present invention to provide modified immunoglobulin formulations that can be made up of immunoglobulin conjugates as discussed in paragraph [0007] and any and all combinations of their embodiments at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin conjugate is at a concentration of greater than the concentration at which an immunoglobulin conjugate known to have a high propensity for oligomerization forms oligomers in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the immunoglobulin conjugate is non-oligomerized monomer. In certain embodiments that may be combined with any of the preceding embodiments, the formulation includes a pharmaceutically acceptable excipient. In certain embodiments that may be combined with any of the preceding embodiments, the immunoglobulin formulation comprises at least eighty percent, at least eighty-five percent, at least ninety percent, at least ninety-five percent, at least ninety-six percent, at least ninety-seven percent, at least ninety-eight percent, or at least ninety-nine percent of immunoglobulin conjugate that is non-oligomerized monomer.

It is accordingly an object of the present invention to provide uses of the immunoglobulin conjugates as discussed in paragraph [0007] and any and all combinations of their embodiments as a non-oligomerizing pharmaceutical active ingredient.

It is accordingly an object of the present invention to provide pharmaceutical compositions that include an immunoglobulin conjugate as discussed in paragraph [0007] and any and all combinations of their embodiments and a pharmaceutically acceptable excipient. In certain embodiments, the immunoglobulin is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin conjugate is at a concentration of greater than the concentration at which an immunoglobulin conjugate known to have a high propensity for oligomerization forms oligomers in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the immunoglobulin conjugate is non-oligomerizing monomer. In certain embodiments that may be combined with any of the preceding embodiments, the immunoglobulin formulation comprises at least eighty percent, at least eighty-five percent, at least ninety percent, at least ninety-five percent, at least ninety-six percent, at least ninety-seven percent, at least ninety-eight percent, or at least ninety-nine percent of immunoglobulin conjugate that is non-oligomerized monomer. In certain embodiments that may be combined with preceding embodiments, the oligomerization is measured by non-reducing SDS-PAGE.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the immunoglobulin conjugate, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an immunoglobulin conjugate of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively an immunoglobulin conjugate of the invention can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of immunoglobulin conjugate of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an immunoglobulin conjugate of the invention can be administered via a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S.

Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

It is accordingly an object of the present invention to provide uses of the immunoglobulin conjugates as discussed in paragraph [0007] and any and all combinations of their embodiments in the preparation of a medicament comprising a highly concentrated liquid formulation wherein the immunoglobulin conjugate concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the use of the medicament is for the treatment of autoimmune diseases, immunological diseases, infectious diseases, inflammatory diseases, neurological diseases, and oncological and neoplastic diseases including cancer. In certain embodiments, the use of the medicament is for the treatment of congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases. In certain embodiments, the use of the medicament is for the treatment of plaque psoriasis, ulcerative colitis, non-Hodgkin's lymphoma, breast cancer, colorectal cancer, juvenile idiopathic arthritis, macular degeneration, respiratory syncytial virus, Crohn's disease, rheumatoid arthritis, psoriatic arthritis, ankylosing spondylitis, osteoporosis, treatment-induced bone loss, bone metastases, multiple myeloma, Alzheimer's disease, glaucoma, and multiple sclerosis. In certain embodiments that may be combined with any of the preceding embodiments, the use of the medicament further comprises a pharmaceutically acceptable excipient. In certain embodiments that may be combined with any of the preceding embodiments, the immunoglobulin conjugate in the medicament shows at least at least eighty percent, at least eighty-five percent, at least ninety percent, at least ninety-five percent, at least ninety-six percent, at least ninety-seven percent, at least ninety-eight percent, or at least ninety-nine percent non-oligomerized monomer. In certain embodiments, the oligomerization is measured by non-reducing SDS-PAGE.

EXAMPLES

The Examples described herein refer to particular, non-limiting embodiments of the invention.

Example 1

Design, Expression, and Conjugation of Antibody Cysteine Variants

A set of IgG1 cysteine variants was designed such that each immunoglobulin fold domain is represented (Table 1). Variants 1-13 were designed from the X-ray structure of antibody-1. Variant 14 was selected from the structure of another IgG1, antibody-2, built by homology modeling with respect to antibody-1. All sites were exposed on the antibody surface. Polar residues, such as serine and threonine and arginine, or charged residues, such as lysine, were substituted with cysteine. The light and heavy chain genes were subcloned in vector gWIZ (Genlantis) and engineered for protein expression by transient transfection of mammalian cells. Antibody variants were either de novo synthesized (GeneArt) or generated by site-directed mutagenic PCR and confirmed by sequencing. Antibody wild type and variants were expressed at 10-100 mg levels by transient transfection of Freestyle HEK 293 cells (Invitrogen) with polyethyleneimine (Polysciences) as the transfection reagent. Cell culture supernatant was collected 7-10 days post-transfection. Antibodies were purified on a protein A column (GE Healthcare), eluted with 50 mM citrate buffer, pH 3.5, and buffer exchange in 100 mM Tris pH 7.0 buffer for fluorescence labeling.

Following expression and purification of antibody variants, the engineered surface cysteines were mostly oxidized. For example both Variant 4 and 6 had less than 0.3 free thiol per antibody molecule as opposed to the anticipated 2.0 for the antibodies with engineered surface cysteines. We compared the effect of a mild reducing agent, TCEP (Tris[2-carboxyethyl]phosphine hydrochloride) and a stronger reducing agent, DTT (dithiothreitol) on a variant from class I and a variant from class IV. Initially, the non-oligomerizing Variant 4 showed 0.13 free thiol per antibody, and the highly oligomerizing Variant 6 had 0.25 free thiol per antibody.

Aliquots of wild type, variant 4, and variant 6 were treated in five different conditions: 1) no reducing agent, 2) TCEP, 10×, 1 hour, 3) TCEP, 20×, 1 hour, 4) DTT, 5×, 15 minutes, and 5) DTT, 10×, 15 minutes. After removal of the reducing agent the samples were resolved on non-reducing PAGE and were quantified for free thiol. A comparison of the results for wild type and variants indicated that the TCEP treatment was sufficient to reduce cysteines in non-oligomerized form (Variant 4) with little effect on WT. However, cysteines from oligomers (Variant 6) were reduced only after a harsher treatment. Treatment with DTT even at low levels leads to antibody fragmentation for WT and both variants. The sites where the surface cysteines were introduced had a profound effect on the ability to decap the engineered cysteines for conjugation.

Different methods were attempted for the specific reduction of the engineered surface thiols before labeling. TCEP and DTT were two of the reagent used, and levels of free thiol were quantified using Ellman's reagent (Invitrogen). We found L-cysteine to work best in our site-specific labeling experiments, so the following two-step protocol was used. First, the variants were incubated with 100-200 fold excess of L-cysteine for 4 hrs at 37° C., followed by buffer exchange into 50 mM Tris/EDTA. Second, the samples were incubated with 5-10 fold excess of ALEXA FLUOR® 488 maleimide dye (Invitrogen) for 1 hr at room temperature or with 10 fold excess of Pyrene maleimide dye (Invitrogen) for 12 hrs at room temperature. After removal of free dye, and buffer exchange to 50 mM phosphate buffer pH 7.0, the efficiency of protein labeling was calculated as mole of dye per mole of protein according to manufacturer's protocols (Invitrogen).

Example 2

Characterization of the Engineered Antibody Cysteine Variants

Unlabeled and labeled antibody samples were analyzed by SDS-PAGE. Gels of 7.5%, 10%, and 12% were used for non-reducing analysis. Gels of 12% were used for reducing analysis of heated samples with DTT. Usually, samples of 5-10 µg were loaded per lane. Fluorescent images were taken under UV light before staining with Coomassie Blue. Antibody digestion was carried out by GluC (1:20 wt enzyme per wt antibody, at 25° C. for 12-24 hrs) and pronase (1:20 wt enzyme per wt antibody, at 37° C. for 1 hr).

Non-reducing gels show monomers as well as the presence of dimers, trimers, and in some cases even higher oligomers. Reducing gels show the exclusive labeling of the light or heavy chain depending on where the surface cysteine was engineered. Labeled and unlabeled variants 1-6 were also analyzed for antigen binding specificity. The variants retain activity within 80% and 130% of wild type with some loss of activity upon labeling. Unlabeled variant 1 retained approximately 110% of wild-type activity, whereas labeled variant 1 retained approximately 80%. Unlabeled variant 2 retained approximately 105% activity of wild-type, whereas labeled variant 2 retained slightly less than 100% activity. Unlabeled and labeled variant 3 both retained approximately 110% of wild-type activity. Unlabeled variant 4 retained approximately 125% of wild-type activity, whereas labeled variant 4 retained approximately 95% of activity. Unlabeled variant 5 retained approximately 120% of wild-type activity, whereas labeled variant 6 retained approximately 100% of activity. Finally, unlabeled variant 6 retained approximately 115% of wild-type activity, whereas labeled variant 6 retained approximately 90% of activity. Similarly to its unlabeled counterpart, labeled variant 6 showed high oligomerization propensity.

Most variants were labeled near the optimal efficiency of 2.0 moles dye per mole antibody (two identical cysteines per antibody molecule). Higher than 2.0 labeling efficiency is non-desirable since that would suggest partial disruptions and labeling of intrachain disulfides. Variants with high oligomerization propensity such as Variant 6, Variant 11 and Variant 5 did not label as efficiently. Even among the other variants, labeling conditions such as time of reaction and dye to protein ratio had to be optimized on an individual basis because not all engineered cysteines were equally amenable to conjugation. Variants 1-14 were specifically labeled at the chain that carries the engineered cysteine. Proteolytic treatment of the variants with pronase yielded different fluorescence patterns for most variants, but similar patterns for variants with neighboring substitutions, such as Variant 3 and 12. Thus, most variants were efficiently and specifically labeled.

Five classes of cross-linking propensity were distinguished for this set of cysteine variants (Table 1). Class I comprises variants that were monomeric and remain stable after labeling. Variants of class II contained a small percent of dimers before and after labeling. Class III variants had a more pronounced propensity to oligomerize including formation of some trimers. Class IV variants had an even higher propensity to oligomerize as evidenced by the presence of aggregates larger than trimer, especially after labeling. Class V included variants of high oligomerization propensity similarly to variant of Class IV with additional structural abnormalities such as fragmentation or coloration of purified concentrated sample.

Example 3

Application of the Engineered Antibody Cysteine Variants

Cysteine variants with low cross-linking propensity (Variants 1-4, 7, 10, 12-14) were labeled with high specificity and efficiency and little oligomerization. Labeling with maleimide dyes is only one example of site-specific conjugation on these antibody variants. Molecules with many other functionalities such as binding specificity or toxicity can be equally attached. Thus, this set of variants expands on the repertoire of antibody variants to serve for payload vehicles in targeted therapy or for in vitro and in vivo fluorescence analysis.

To illustrate the fluorescence application of one of the variants, we analyzed the emission pattern of variants conjugated with the fluorophore pyrene. When two pyrene molecules are close together there is a characteristic increase of emission at 465 nm known as excimer fluorescence. We labeled Variants 4 and 7 with pyrene maleimide and monitored emission spectra. While Variant 4 showed basal level emission at 465 nm, Variant 7 showed strong excimer fluorescence. Considering the position of the engineered cysteine in $C_H1$ for Variant 7, on the inner side of the Fab domains, the observed result correlates with the known scissoring effect of the Fab's with respect to Fc. Thus, this variant can be used in the analysis of antibody domain dynamics.

The high oligomerization propensity of Variant 6 suggested another utility of antibody cysteine variants that was explored in greater detail. Labeled variant 6 was subjected to gel filtration chromatography in order to separate monomer from oligomers, and protein-containing fractions were resolved on a 7.5% non-reducing SDS-PAGE gel and analyzed before and after staining with Coomasssie Blue. The gel filtration analysis on variant 6 indicated a competition between labeling and crosslinking: the higher the MW of the species, the lower the labeling efficiency (indicated by the level of fluorescence). The highest MW species had a labeling efficiency of 0.5, while the monomeric species had a labeling efficiency of 1.0, with the original labeled sample of labeling efficiency 0.8. An antibody variant with multiple oligomers, Variant 6 presents an excellent control for antibody oligomerization and a suitable standard for high molecular weight proteins, with the additional functionality that it can be site-specifically labeled.

Example 4

Correlation Between Cross-Linking Propensity (CLP) and Spatial-Aggregation Propensity (SAP) of the Cysteine Variants Cross-linking propensity (CLP) and spatial aggregation propensity (SAP) were compared for the cysteine variants where specific amino acids are substituted with cysteine. Each variant was assigned CLP based on non-reducing SDS-PAGE analysis. SAP values for the mutated residues are from computational results with radius of 5 Å. We overlaid the engineered cysteine variants on the SAP-coded antibody-1 structure.

The following correlations were observed. All amino acids substituted with cysteines are of negative SAP-value in the range from −0.27 to 0.00. This is consistent with the choice of polar or charged amino acids for substitution. All variants of CLP class I have SAP between 0.00 and −0.11 (Variants 3, 4, 7, 10, 12), and all variants of CLP class II have SAP between −0.12 and −0.23 (Variants 1, 2, 13). However, there are variants with SAP in those ranges with high CLP (Variants 8, 9 and 11 for example). The highly cross-linking variants Variant 8 and 11 neighbor high-SAP sites. Variant 5 with CLP III is adjacent to high-SAP sites in $C_H2$, while Variant 2 of CLP II is not. However, there is no such correlation between Variant 6 and Variant 10 in $C_H3$, and between Variant 9 and 14 in $V_H$.

An additional observation was made of Variant 14. Variant 14 fails to express if there is a region of high SAP nearby, whereas it expresses when this high SAP region is replaced by a region of low SAP. A 100-fold higher yield of Variant 14 in the stabilized antibody-2 (35.6 mg/L culture) was observed compared to that of Variant 14 in the native antibody-2 background (0.34 mg/L). The relative yield of Variant 14 in the different backgrounds indicated a structural problem when a cysteine is introduced on the surface of a protein near a region of high SAP value. The problem was resolved when two hydrophobic amino acids in the hydrophobic patch neighboring the engineered cysteine were substituted with lysines.

In summary, correlations exist between stability of cysteine variants and SAP: 1) cysteine variants with low cross-linking propensity have slightly negative SAP (0.00 to −0.11), 2) cysteine variants with more negative SAP (−0.12 to −0.23) are more prone to cross-linking, and 3) cysteine variants in immediate proximity to patches of high-SAP are more likely to cross-link or have structural abnormalities. Conclusions 1 and 2 are consistent with the previously defined notion that fully exposed residues may be more susceptible to cross-linking [9].

Example 5

Conclusion

We designed a set of human IgG1 cysteine variants that are broadly distributed on the antibody molecule with at least one variant per immunoglobulin fold domain. Most of these variants are stable, and can be conjugated efficiently and specifically without significant loss of antigen binding activity. Thus, the stable antibody variants add to the repertoire of variants for site-specific conjugation of payload molecules. If fluorophores are attached to the engineered cysteines, the dynamics of particular domains can be analyzed. The highly oligomerizing variants are beneficial as well, as the numerous multimers provide a convenient standard for antibody aggregates and for high molecular weight proteins in general.

A correlation between the cross-linking propensity of the antibody cysteine variants described here and the SAP method demonstrate that the SAP methodology may be used to screen for conjugation sites with reduced cross-linking. The SAP technology is computer-based, so it reduces the time and experimental work in variants design. CLP/SAP comparison showed that substitution of partially and not fully exposed amino acids yields the most stable variants. Moreover, the comparison showed that neighboring hydrophobic patches should be avoided.

The engineered human IgG1 surface cysteine variants described here provide new sites for site-specific conjugation of therapeutic antibodies and methods for identifying further variants. The variants with little crosslinking propensity have the greatest utility in developing antibodies for targeted therapy. The cysteine variants disclosed herein include new sites in previously represented domains ($C_L$, $C_H1$, $C_H3$) as well as in previously unrepresented domains ($V_L$, $V_H$, $C_H2$).

Moreover, the labeled variants can be used as a set of site-specific fluorescent antibody markers for in vitro and in vivo laboratory research. The fluorescently labeled products can be commercialized via biotechnology companies (such as Thermo Scientific Pierce, GE Healthcare, and Invitrogen) providing the research community with antibody and other protein reagents.

The highly cross-linking variant 6 is a useful protein-gel or other chromatography technique standard. It can be marketed by companies (for example Invitrogen, Bio-Rad, and Pierce) providing protein reagents.

The correlation between CLP and SAP further suggested a commercial application of our previously described SAP technology. Consideration of SAP can improve the design of stable antibody cysteine variants for site-specific conjugation.

TABLE 1

| Variant | Domain | Residue | CLP | SAP |
|---------|--------|---------|-----|------|
| 1 | CH2 | K248 | II | −0.12 |
| 2 | CH2 | K326 | II | −0.19 |
| 3 | VL | T22 | I | −0.07 |
| 4 | CL | T197 | I | −0.03 |
| 5 | CH2 | N286 | III | −0.27 |
| 6 | CH3 | S440 | IV | −0.09 |
| 7 | CH1 | S125 | I | −0.06 |
| 8 | CH2 | S298 | V | −0.19 |
| 9 | VH | S25 | III | −0.07 |
| 10 | CH3 | S442 | I | 0.00 |
| 11 | CH2 | S254 | V | −0.06 |
| 12 | VL | T20 | I | −0.04 |
| 13 | CH3 | S415 | II | −0.23 |
| 14 | VH | S7 | I | −0.11 |

REFERENCES

1. Carter, P. J., Potent antibody therapeutics by design. Nat Rev Immunol, 2006. 6(5): p. 343-57.

2. Polakis, P., Arming antibodies for cancer therapy. Curr Opin Pharmacol, 2005. 5(4): p. 382-7.
3. Kaminski, M. S., et al., Radioimmunotherapy of B-cell lymphoma with [131I]anti-B1 (anti-CD20) antibody. N Engl J Med, 1993. 329(7): p. 459-65.
4. King, D. J., et al., Preparation and preclinical evaluation of humanised A33 immunoconjugates for radioimmunotherapy. Br J Cancer, 1995. 72(6): p. 1364-72.
5. Khaw, B. A., et al., Myocardial infarct imaging of antibodies to canine cardiac myosin with indium-111-diethylenetriamine pentaacetic acid. Science, 1980. 209 (4453): p. 295-7.
6. Rodwell, J. D., et al., Site-specific covalent modification of monoclonal antibodies: in vitro and in vivo evaluations. Proc Natl Acad Sci USA, 1986. 83(8): p. 2632-6.
7. Sun, M. M., et al., Reduction-alkylation strategies for the modification of specific monoclonal antibody disulfides. Bioconjug Chem, 2005. 16(5): p. 1282-90.
8. Junutula, J. R., et al., Site-specific conjugation of a cytotoxic drug to an antibody improves the therapeutic index. Nat Biotechnol, 2008. 26(8): p. 925-32.
9. Lyons, A., et al., Site-specific attachment to recombinant antibodies via introduced surface cysteine residues. Protein Eng, 1990. 3(8): p. 703-8.
10. Shopes, B., A genetically engineered human IgG mutant with enhanced cytolytic activity. J Immunol, 1992. 148 (9): p. 2918-22.
11. Shopes, B., A genetically engineered human IgG with limited flexibility fully initiates cytolysis via complement. Mol Immunol, 1993. 30(6): p. 603-9.
12. Stimmel, J. B., et al., Site-specific conjugation on serine right-arrow cysteine variant monoclonal antibodies. J Biol Chem, 2000. 275(39): p. 30445-50.
13. Zheng, Y., et al., Conformations of IgE bound to its receptor Fc epsilon RI and in solution. Biochemistry, 1991. 30(38): p. 9125-32.
14. Zheng, Y., et al., Dynamic conformations compared for IgE and IgG1 in solution and bound to receptors. Biochemistry, 1992. 31(33): p. 7446-56.
15. Junutula, J. R., et al., Rapid identification of reactive cysteine residues for site-specific labeling of antibody-Fabs. J Immunol Methods, 2008. 332(1-2): p. 41-52.

What we claim is:

1. An immunoglobulin conjugate, comprising A) an immunoglobulin having light chain variable region a mutation at residue 22($V_L$), wherein the residue numbering for the immunoglobulin is according to Kabat numbering, wherein the mutation is a substitution with a cysteine residue, and B) an atom or molecule, wherein the atom or molecule is conjugated to the cysteine residue.

2. The immunoglobulin conjugate of claim 1, further comprising a linker molecule having at least two reactive sites, wherein a first reactive site is bound to the cysteine residue of the immunoglobulin and a second reactive site is bound to the atom or molecule.

3. The immunoglobulin conjugate of claim 2, wherein the linker molecule is selected from the group consisting of a hydrazone, a peptide, a chelating agent, and a maleimide.

4. The immunoglobulin conjugate of claim 2, wherein the linker molecule forms a disulfide linkage with the cysteine residue.

5. The immunoglobulin conjugate of claim 1, wherein the atom or molecule is selected from the group consisting of a radionuclide, a chemotherapeutic agent, a microbial toxin, a plant toxin, a polymer, a carbohydrate, a cytokine, a fluorescent label, a luminescent label, an enzyme-substrate label, an enzyme, a peptide, a peptidomimetic, a nucleotide, an siRNA, a microRNA, an RNA mimetic, and an aptamer.

6. The immunoglobulin conjugate of claim 1, wherein the atom or molecule is selected from the group consisting of $^{90}$Y, $^{131}$I, $^{67}$Cu, $^{177}$Lu, $^{213}$Bi, $^{211}$At, a calicheamicin, a duocarmycin, a maytanisoid, an auristatin, an anthracyclin, *Pseudomonas* exotoxin A, Diphtheria toxin, ricin, polyethylene glycol, hydroxyethyl starch, and a mannosyl residue.

7. A modified or isolated immunoglobulin comprising a light chain variable region mutation at residue 22($V_L$), wherein the residue numbering for the immunoglobulin is according to Kabat numbering, wherein the mutation is a substitution with a cysteine residue.

8. A pharmaceutical composition comprising the immunoglobulin conjugate of claim 1 and a pharmaceutically acceptable excipient, wherein at least eighty percent, at least eighty-five percent, at least ninety percent, at least ninety-five percent, at least ninety-six percent, at least ninety-seven percent, at least ninety-eight percent, or at least ninety-nine percent of the immunoglobulin conjugate is non-oligomerized monomer.

9. The pharmaceutical composition of claim 8, wherein the immunoglobulin conjugate is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

* * * * *